(12) United States Patent
Cao et al.

(10) Patent No.: US 8,609,612 B2
(45) Date of Patent: Dec. 17, 2013

(54) METHODS OF TREATING GLUCOSE METABOLISM DISORDERS

(75) Inventors: Zhaodan Cao, San Antonio, TX (US); Yarong Lu, Watertown, MA (US); Daniel David Kaplan, San Mateo, CA (US)

(73) Assignee: NGM Biopharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 13/577,641

(22) PCT Filed: Feb. 7, 2011

(86) PCT No.: PCT/US2011/023916
§ 371 (c)(1),
(2), (4) Date: Sep. 5, 2012

(87) PCT Pub. No.: WO2011/100197
PCT Pub. Date: Aug. 18, 2011

(65) Prior Publication Data
US 2013/0017994 A1 Jan. 17, 2013

Related U.S. Application Data

(60) Provisional application No. 61/304,264, filed on Feb. 12, 2010.

(51) Int. Cl.
*A01N 47/00* (2006.01)
(52) U.S. Cl.
USPC .......................................................... 514/6.7
(58) Field of Classification Search
None
See application file for complete search history.

(56) References Cited

U.S. PATENT DOCUMENTS

| | | | |
|---|---|---|---|
| 3,892,311 A * | 7/1975 | Sneider | 206/229 |
| 6,506,607 B1 | 1/2003 | Shyjan | |
| 6,902,911 B1 | 6/2005 | Conklin | |
| 7,312,079 B1 * | 12/2007 | Hu | 435/325 |
| 2005/0118625 A1 | 6/2005 | Mounts | |
| 2007/0048301 A1 | 3/2007 | Bodary-Winter et al. | |
| 2007/0089176 A1 * | 4/2007 | Zoephel et al. | 800/14 |
| 2007/0224644 A1 | 9/2007 | Liotta et al. | |
| 2008/0070797 A1 | 3/2008 | Mounts | |
| 2009/0138977 A1 | 5/2009 | Domon et al. | |
| 2009/0226897 A1 | 9/2009 | Davies et al. | |
| 2009/0325810 A1 | 12/2009 | Lapointe et al. | |

FOREIGN PATENT DOCUMENTS

WO  WO 2009028880  3/2009

OTHER PUBLICATIONS

Cho et al. (2009) "A Large-Scale Genome-Wide Association Study of Asian Populations Uncovers Genetic Factors Influencing Eight Quantitative Traits" *Nat. Genet.* 41(5):527-534.
GenBank Accession No. NM_001040020 "*Homo sapiens* family with sequence similarity 3, member C (FAM3C), transcript variant 2, mRNA" dated Feb. 7, 2010.
GenBank Accession No. NM_001099147 "*Bos taurus* family with sequence similarity 3, member C (FAM3C), mRNA" dated Feb. 9, 2008.

(Continued)

*Primary Examiner* — Karlheinz R Skowronek
*Assistant Examiner* — Khalid Kader
(74) *Attorney, Agent, or Firm* — Paula A. Borden; Carol L. Francis; Bozicevic, Field & Francis LLP.

(57) ABSTRACT

Methods of treating individuals with a glucose metabolism disorder, and compositions thereof, are provided.

12 Claims, 11 Drawing Sheets

(56) References Cited

OTHER PUBLICATIONS

GenBank Accession No. NM_014888 "*Homo sapiens* family with sequence similarity 3, member C (FAM3C), transcript variant 1, mRNA" dated Jan. 31, 2010.
GenBank Accession No. NM_138587.4 "*Mus musculus* family with sequence similarity 3, member C (Fam3c), mRNA" dated Sep. 3, 2009.
GenBank Accession No. NM_198771.1 "*Rattus norvegicus* family with sequence similarity 3, member C (Fam3c), mRNA" dated Feb. 11, 2008.
GenBank Accession No. NP_001035109 "family with sequence similarity 3, member C precursor [*Homo sapiens*]" dated Feb. 7, 2010.
GenBank Accession No. NP_001092617 "family with sequence similarity 3, member C [*Bos taurus*]" dated Feb. 9, 2008.
GenBank Accession No. NP_055703 "family with sequence similarity 3, member C precursor [*Homo sapiens*]" dated Jan. 31, 2010.
GenBank Accession No. NP_613053.3 "D6Wsul76e protein precursor [*Mus musculus*]" dated Sep. 3, 2009.
GenBank Accession No. NP_942066.1 "family with sequence similarity 3, member C [*Rattus norvegicus*]" dated Feb. 11, 2008.
Grønborg et al. (2006) "Biomarker discovery from pancreatic cancer secretome using a differential proteomic approach" *Mol. Cell Proteomics* 5(1):157-171.
Guo et al. (2006) "GG: A Domain Involved in Phage LTF Apparatus and Implicated in Human MEB and Non-Syndromic Hearing Loss Diseases" *FEBS Lett.* 580(2):581-584.
Lahsnig et al. (2009) "ILEI Requires Oncogenic Ras for the Epithelial to Mesenchymal Transition of Hepatocytes and Liver Carcinoma Progression" *Oncogene* 28(5):638-650.
Lee et al. (2009) "The *Mycobacterium bovis* Bacille Calmette-Guerin Phagosome Proteome" *Mol. Cell Proteomics* 9(1):32-53.
Mauri et al. (2005) "Identification of Proteins Released by Pancreatic Cancer Cells by Multidimensional Protein Identification Technology: A Strategy for Identification of Novel Cancer Markers" *FASEB J.* 19(9):1125-1127.
Pilipenko et al. (2004) "Genomic Organization and Expression Analysis of the Murine Fam3c Gene" *Gene* 335:159-168.
Waerner et al. (2006) "ILEI: A Cytokine Essential for EMT, Tumor Formation, and Late Events in Metastasis in Epithelial Cells" *Cancer Cell* 10(3):227-239.
Xiao et al. (2009) "Proteomic Analysis of Cerebrospinal Fluid from Patients with Idiopathic Temporal Lobe Epilepsy" *Brain Res.* 1255:180-189.
Zhu et al. (2002) "Cloning, Expression, and Initial Characterization of a Novel Cytokine-Like Gene Family" *Genomics* 80:144.
Wang et al. (2008) "Mechanisms of Glucose-Induced Expression of Pancreatic-Derived Factor in Pancreatic β-Cells" *Endocrinology* 149(2):672-680.
GenBank Accession No. BAA13251 "GS3786 [*Homo sapiens*]" dated Mar. 11, 1998.
Ota et al. (2004) "Complete sequencing and characterization of 21,243 full-length human cDNAs" *Nat Genet* 36(1):40-45.

\* cited by examiner

\* p<0.05
\*\* p<0.01
\*\*\* p<0.001
Fam3C vs. GFP

\*　　p<0.05
\*\*　　p<0.01
\*\*\*　p<0.001
Fam3C vs. GFP

\* p<0.05
\*\* p<0.01
\*\*\* p<0.001
hFAM3C vs. GFP

\*     p<0.05  
\*\*    p<0.01  
\*\*\*   p<0.001  
hFAM3C vs. GFP

\*    p<0.05
\*\*   p<0.01
\*\*\* p<0.001
hFAM3C vs. GFP

\*     p<0.05
\*\*    p<0.01
\*\*\*   p<0.001
hFAM3C vs. GFP

\*     p<0.05
\*\*    p<0.01
\*\*\*   p<0.001
hFAM3C vs. GFP

Figure 11

```
human   MRVAGAAKLVVAVAVFLLIFYVISQVFEIKMDASLGNLFARSALDTAARSTKPPRYKCGI 60
murine  MRVAGAAKLVVAVAVFLLTFYVISQVFEIKMDASLGNLFARSALDSAIRSTKPPRYKCGI 60
bovine  MRVAGAAKLVVAVAVFLLTFYVISQVFEIKMDASLGNLFARSALDAVVRSTKPPRYKCGI 60
        ************************************************:. ********* human   SKACPEKHFAFKMASGAANVVGPKICLEDNVLMSGVKNNVGRGINVALANGKTGEVLDTK 120
murine  SKACPEKHFAFKMASGAANVVGPKICLEDNVLMSGVKNNVGRGINIALVNGKTGEVIDTK 120
bovine  SKACPEKHFAFKMASGAANVVGPKICLEDNVLMSGVKNNVGRGINVALVNGKTGELIDTR 120
        *********************************************:**.******::**:

human   YFDMWGGDVAPFIEFLKAIQDGTIVLMGTYDDGATKLNDEARRLIADLGSTSITNLGFRD 180
murine  FFDMWGGDVAPFIEFLKTIQDGTVVLMATYDDGATKLTDEARRLIAELGSTSITSLGFRD 180
bovine  FFDMWGGNVAPFIEFLKAIQDGTIVLMGTYDDGATKLNDEARRLIAELGSTSITHLGFRD 180
        :****:****:*:*.******.****:***  *** human   NWVFCGGKGIKTKSPFEQHIKNNKDTNKYEGWPEVVEMEGCIPQKQD 227
murine  NWVFCGGKGIKTKSPFEQHIKNNKETNKYEGWPEVVEMEGCIPQKQD 227
bovine  NWVFCGGKGIKTKSPFEQHIKNNKDTNKYEGWPEVVEMEGCIPQKQD 227
        ***********************:***********************
```

METHODS OF TREATING GLUCOSE METABOLISM DISORDERS

CROSS-REFERENCE TO RELATED APPLICATIONS

This application claims priority benefit of U.S. provisional application Ser. No. 61/304,264, filed Feb. 12, 2010, which application is incorporated herein by reference in its entirety.

INTRODUCTION

High blood glucose levels stimulate the secretion of insulin by pancreatic beta-cells. Insulin in turn stimulates the entry of glucose into muscles and adipose cells, leading to the storage of glycogen and triglycerides and to the synthesis of proteins. Activation of insulin receptors on various cell types diminishes circulating glucose levels by increasing glucose uptake and utilization, and by reducing hepatic glucose output. Disruptions within this regulatory network can result in diabetes and associated pathologic syndromes that affect a large and growing percentage of the human population.

Patients who have a glucose metabolism disorder can suffer from hyperglycemia, hyperinsulinemia, and/or glucose intolerance. An example of a disorder that is often associated with the aberrant levels of glucose and/or insulin is insulin resistance, in which fliver, fat, and muscle cells lose their ability to respond to normal blood insulin levels.

Therapy that can modulate glucose and/or insulin levels in a patient and to enhance the biological response to fluctuating glucose levels remains of interest.

SUMMARY OF THE INVENTION

The present disclosure provides compositions that find use in modulating glucose and/or insulin levels in glucose metabolism disorders. The present methods involve using an isolated protein FAM3C (Family with sequence similarity 3, member C) for modulating glucose metabolism. The protein may be used as therapy to treat various glucose metabolism disorders, such as diabetes mellitus, and/or obesity. The subject proteins encompass those expressed by FAM3C genes, and homologues thereof, and are useful for but not limited to treating one or more of the following conditions: diabetes mellitus (e.fg. diabetes type I, diabetes type II and gestational diabetes), insulin resistance, hyperinsulinemia, glucose intolerance, hyperglycemia or metabolic syndrome.

BRIEF DESCRIPTION OF THE DRAWINGS

FIG. 11 shows an alignment of various amino acid sequences of FAM3C.

Figure 1:
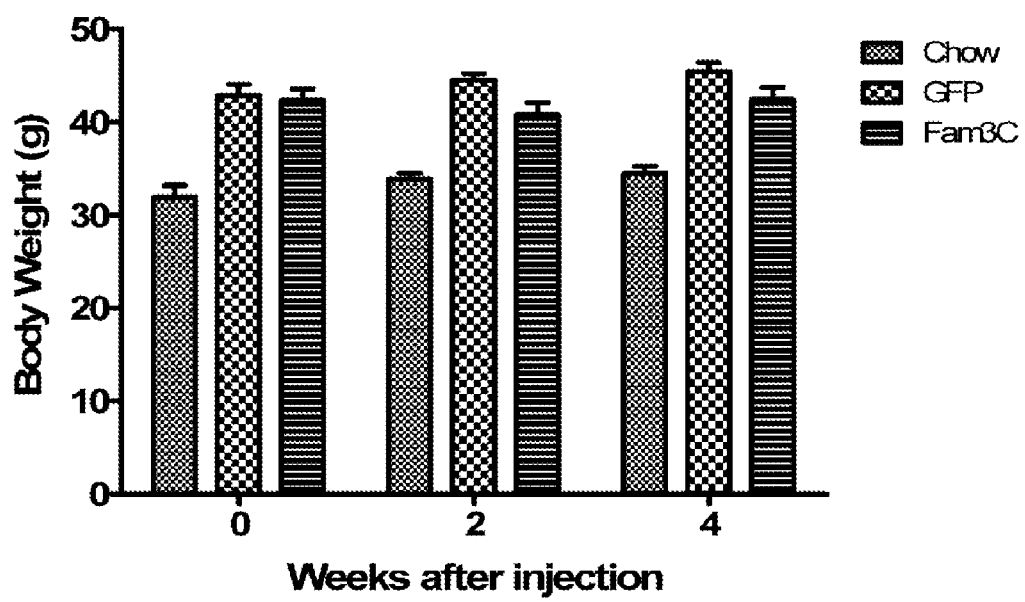
FIG. 1 shows body weight of mice on a high fat diet that were injected with an adeno-associated virus (AAV) expressing a protein of the present disclosure (mouse ortholog) compared to those of mice injected with a control virus and those on a lean diet (n=5 mice per group).

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "the protein" includes reference to one or more proteins, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

Overview

The present disclosure provides compositions that find use in modulating glucose and/or insulin levels in glucose metabolism disorders. The compositions encompass FAM3C (Family with sequence similarity 3, member C), genes and/or proteins encoded thereby, and are useful for but not limited to treating diabetes mellitus (e.g. diabetes type I, diabetes type II, and gestational diabetes). In a diet-induced obesity model (mice on a high fat diet), the glucose and insulin levels are higher than those in a subject on a regular lean diet. However, when treated with AAV expressing the proteins of the present disclosure, the subject on the high fat diet regains the ability to regulate glucose levels, to an extent seen in subjects on a regular lean diet. Accordingly, the proteins of the present disclosure may be used in restoring glucose homeostasis in subjects with a dysfunctional glucose metabolism, including subjects who may be overweight, obese, and/or on a high fat diet.

Definitions

The terms "patient" or "subject" as used interchangeably herein in the context of therapy, refer to a human and non-human animal, as the recipient of a therapy or preventive care.

The phrase "in a sufficient amount to effect a change in" means that there is a detectable difference between a level of an indicator measured before and after administration of a particular therapy. Indicators include but are not limited to glucose and insulin.

The phrase "glucose tolerance", as used herein, refers to the ability of a subject to control the level of plasma glucose and/or plasma insulin when glucose intake fluctuates. For example, glucose tolerance encompasses the ability to reduce the level of plasma glucose back to a level before the intake of glucose within about 120 minutes or so.

The phrase "pre-diabetes", as used herein, refers a condition that may be determined using either the fasting plasma glucose test (FPG) or the oral glucose tolerance test (OGTT). Both require a person to fast overnight. In the FPG test, a person's blood glucose is measured first thing in the morning before eating. In the OGTT, a person's blood glucose is checked after fasting and again 2 hours after drinking a glucose-rich drink. In a healthy individual, a normal test result of FPG would indicate a glucose level of below about 100 mg/dl. A subject with pre-diabetes would have a FPG level between about 100 and about 125 mg/dl. If the blood glucose level rises to about 126 mg/dl or above, the subject is determined to have "diabetes". In the OGTT, the subject's blood glucose is measured after a fast and 2 hours after drinking a glucose-rich beverage. Normal blood glucose in a healthy individual is below about 140 mg/dl 2 hours after the drink. In a pre-diabetic subject, the 2-hour blood glucose is about 140 to about 199 mg/dl. If the 2-hour blood glucose rises to 200 mg/dl or above, the subject is determined to have "diabetes".

"FAM3C" (Family with sequence similarity 3, member C), also known as "GS3786" or "ILEI" ("interleukin-related protein interleukin-like EMT inducer"), encompasses murine and human proteins that are encoded by gene FAM3C or a gene homologue of FAM3C. FAM3C is found in many mammals (e.g. human, non-human primates, canines, and mouse). See FIG. 11 for alignments of various amino acid sequences of FAM3C.

As used herein, "homologues" or "variants" refers to protein or DNA sequences that are similar based on their amino acid or nucleic acid sequences, respectively. Homologues or variants encompass naturally occurring DNA sequences and proteins encoded thereby and their isoforms. The homologues also include known allelic or splice variants of a protein/gene. Homologues and variants also encompass nucleic acid sequences that vary in one or more bases from a naturally-occurring DNA sequence but still translate into an amino acid sequence that correspond to the naturally-occurring protein due to degeneracy of the genetic code. Homologues and variants may also refer to those that differ from the naturally-occurring sequences by one or more conservative substitutions and/or tags and/or conjugates.

The terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

It will be appreciated that throughout this present disclosure reference is made to amino acids according to the single letter or three letter codes. For the reader's convenience, the single and three letter amino acid codes are provided below:

| | | |
|---|---|---|
| G | Glycine | Gly |
| A | Alanine | Ala |
| L | Leucine | Leu |
| M | Methionine | Met |
| F | Phenylalanine | Phe |
| W | Tryptophan | Trp |
| K | Lysine | Lys |
| Q | Glutamine | Gln |
| E | Glutamic Acid | Glu |
| S | Serine | Ser |
| P | Proline | Pro |
| V | Valine | Val |
| I | Isoleucine | Ile |
| C | Cysteine | Cys |
| Y | Tyrosine | Tyr |
| H | Histidine | His |
| R | Arginine | Arg |
| N | Asparagine | Asn |
| D | Aspartic Acid | Asp |
| T | Threonine | Thr |

The terms "nucleic acid molecule" and "polynucleotide" are used interchangeably and refer to a polymeric form of nucleotides of any length, either deoxyribonucleotides or ribonucleotides, or analogs thereof. Non-limiting examples of polynucleotides include linear and circular nucleic acids, messenger RNA (mRNA), cDNA, recombinant polynucleotides, vectors, probes, and primers.

The term "heterologous" refers to two components that are defined by structures derived from different sources. For example, where "heterologous" is used in the context of a polypeptide, where the polypeptide includes operably linked amino acid sequences that can be derived from different polypeptides (e.g., a first component consisting of a recombinant peptide and a second component derived from a native FAM3C polypeptide). Similarly, "heterologous" in the context of a polynucleotide encoding a chimeric polypeptide includes operably linked nucleic acid sequence that can be derived from different genes (e.g., a first component from a nucleic acid encoding a peptide according to an embodiment disclosed herein and a second component from a nucleic acid encoding a carrier polypeptide). Other exemplary "heterologous" nucleic acids include expression constructs in which a nucleic acid comprising a coding sequence is operably linked to a regulatory element (e.g., a promoter) that is from a genetic origin different from that of the coding sequence (e.g., to provide for expression in a host cell of interest, which may be of different genetic origin relative to the promoter, the coding sequence or both). For example, a T7 promoter operably linked to a polynucleotide encoding a FAM3C polypeptide or domain thereof is said to be a heterologous nucleic acid. "Heterologous" in the context of recombinant cells can refer to the presence of a nucleic acid (or gene product, such as a polypeptide) that is of a different genetic origin than the host cell in which it is present.

The term "operably linked" refers to functional linkage between molecules to provide a desired function. For example, "operably linked" in the context of nucleic acids refers to a functional linkage between nucleic acids to provide a desired function such as transcription, translation, and the like, e.g., a functional linkage between a nucleic acid expression control sequence (such as a promoter, signal sequence, or array of transcription factor binding sites) and a second polynucleotide, wherein the expression control sequence affects transcription and/or translation of the second polynucleotide. "Operably linked" in the context of a polypeptide refers to a functional linkage between amino acid sequences (e.g., of different domains) to provide for a described activity of the polypeptide.

As used herein in the context of the structure of a polypeptide, "N-terminus" and "C-terminus" refer to the extreme amino and carboxyl ends of the polypeptide, respectively, while "N-terminal" and "C-terminal" refer to relative positions in the amino acid sequence of the polypeptide toward the N-terminus and the C-terminus, respectively, and can include the residues at the N-terminus and C-terminus, respectively. "Immediately N-terminal" or "immediately C-terminal" refers to a position of a first amino acid residue relative to a second amino acid residue where the first and second amino acid residues are covalently bound to provide a contiguous amino acid sequence.

"Derived from" in the context of an amino acid sequence or polynucleotide sequence (e.g., an amino acid sequence "derived from" a FAM3C polypeptide) is meant to indicate that the polypeptide or nucleic acid has a sequence that is based on that of a reference polypeptide or nucleic acid (e.g., a naturally occurring FAM3C polypeptide or FAM3C-encoding nucleic acid), and is not meant to be limiting as to the source or method in which the protein or nucleic acid is made.

"Isolated" refers to a protein of interest that, if naturally occurring, is in an environment different from that in which it may naturally occur. "Isolated" is meant to include proteins that are within samples that are substantially enriched for the protein of interest and/or in which the protein of interest is partially or substantially purified. Where the protein is not naturally occurring, "isolated" indicates the protein has been separated from an environment in which it was made by either synthetic or recombinant means.

"Enriched" means that a sample is non-naturally manipulated (e.g., by an experimentalist or a clinician) so that a protein of interest is present in a greater concentration (e.g., at least a three-fold greater, at least 4-fold greater, at least 8-fold greater, at least 64-fold greater, or more) than the concentration of the protein in the starting sample, such as a biological sample (e.g., a sample in which the protein naturally occurs or in which it is present after administration), or in which the protein was made (e.g., as in a bacterial protein and the like).

"Substantially pure" indicates that an entity (e.g., polypeptide) makes up greater than about 50% of the total content of the composition (e.g., total protein of the composition) and typically, greater than about 60% of the total protein content. More typically, a "substantially pure" refers to compositions in which at least 75%, at least 85%, at least 90% or more of the total composition is the entity of interest (e.g. 95%, of the total protein. Preferably, the protein will make up greater than about 90%, and more preferably, greater than about 95% of the total protein in the composition.

FAM3C

The subject proteins find use in regulating levels of glucose and insulin in a subject. Such proteins find use in treating and/or preventing aberrant levels of glucose and insulin, even if the subject has or has been on a high-fat diet.

The present disclosure provides the use of proteins encompassing naturally-occurring full-length and/or fragments of an amino acid sequence of a FAM3C polypeptide and homologues from different species, and use of such proteins in preparation of formulation for therapy and in methods of treating glucose imbalance in a patient. Exemplary embodiments of such are described below.

"FAM3C", as used in the method of the present disclosure is also known as "family with sequence similarity 3, member C". FAM3C encompasses murine and human variants that are encoded by the FAM3C gene or a gene homologous to FAM3C.

FAM3C refers to FAM3C proteins or FAM3C DNA sequences, which encompass their naturally occurring isoforms and/or allelic/splice variants. A FAM3C protein also refers to proteins that have one or more alteration in the amino acid residues (e.g. at locations that are not conserved across variants and/or species) while retaining the conserved domains and having the same biological activity as the naturally-occurring FAM3C. FAM3C also encompasses nucleic acid sequences that vary in one or more bases from a naturally-occurring DNA sequence but still translate into an amino acid sequence that correspond to the a naturally-occurring protein due to degeneracy of the genetic code. For example, FAM3C may also refer to those that differ from the naturally-occurring sequences of FAM3C by one or more conservative substitutions and/or tags and/or conjugates.

Proteins used in the method of the present disclosure contain contiguous amino acid residues of a length derived from FAM3C. A sufficient length of contiguous amino acid residues may vary depending on the specific naturally-occurring amino acid sequence from which the protein is derived. For example, the protein may be at least 100 amino acids to 150 amino acid residues in length, at least 150 amino acids to 200 amino acid residues in length, or at least 220 amino acids up to the full-length protein (e.g., 223 amino acids, 224 amino acids, 227 amino acids). For example, the protein may be of about 224 amino acid residues in length when derived from a human FAM3C protein, or of about 223 amino acid residues in length when derived from a mouse FAM3C protein.

A protein containing an amino acid sequence that is substantially similar to the amino acid sequence of a FAM3C polypeptide includes a polypeptide comprising an amino acid sequence having at least about 71%, at least about 75%, at least about 80%, at least about 85%, at least about 90%, at least about 95%, at least about 98%, or at least about 99%, amino acid sequence identity to a contiguous stretch of from about 100 amino acids (aa) to about 150 aa, from about 150 aa to about 200 aa, from about 200 aa to about 220 aa, or from about 220 aa up to the full length of a naturally occurring FAM3C polypeptide. For example, a FAM3C polypeptide suitable for use in a subject method can comprise an amino acid sequence having at least about 75%, at least about 80%, at least about 85%, at least about 90%, at least about 94%, at least about 95%, at least about 98%, or at least about 99%, amino acid sequence identity to a contiguous stretch of from about 100 amino acids (aa) to about 150 aa, from about 150 aa to about 200 aa, from about 200 aa to about 220 aa, or from about 220 aa up to the full length, of the human FAM3C polypeptide amino acid sequence depicted in FIG. 11.

The protein may lack at least 5, at least 10, up to at least 50 or more aa relative to a naturally-occurring full-length FAM3C polypeptide. For example, the protein may not contain the signal sequence of based on the amino acid sequence of a naturally-occurring FAM3C polypeptide. The protein may also contain the same or similar glycosylation pattern as those of a naturally-occurring FAM3C polypeptide, may contain no glycosylation, or the glycosylation pattern of host cells used to produce the protein.

Many DNA and protein sequences of FAM3C are known in the art and certain sequences are discussed later below.

The proteins used in the method of the present disclosure include those containing contiguous amino acid sequences of any naturally-occurring FAM3C, as well as those having 1, 2, 3, 4, 5, 6, 7, 8, 9, or 10 usually no more than 20, 10, or 5 amino acid substitutions, where the substitution is usually a conservative amino acid substitution. By "conservative amino acid substitution" generally refers to substitution of amino acid residues within the following groups:
1) L, I, M, V, F;
2) R, K;
3) F, Y, H, W, R;
4) G, A, T, S;
5) Q, N; and
6) D, E.

Conservative amino acid substitutions in the context of a peptide or a protein disclosed herein are selected so as to preserve putative activity of the protein. Such presentation may be preserved by substituting with an amino acid with a side chain of similar acidity, basicity, charge, polarity, or size to the side chain of the amino acid being replaced. Guidance for substitutions, insertion, or deletion may be based on alignments of amino acid sequences of different variant proteins or proteins from different species. For example, according to the alignment shown in FIG. 11, at certain residue positions that are fully conserved (*), substitution, deletion or insertion may not be allowed while at other positions where one or more residues are not conserved, an amino acid change can be tolerated. Residues that are semi-conserved (. or :) may tolerate changes that preserve charge, polarity, and/or size.

The present disclosure provides any of the FAM3C polypeptides described above. The protein may be isolated from a natural source, e.g., is in an environment other than its naturally-occurring environment. The subject protein may also be recombinantly made, e.g., in a genetically modified host cell (e.g., bacteria; yeast; *Pichia*; insect; mammalian cells; and the like), where the genetically modified host cell is genetically modified with a nucleic acid comprising a nucleotide sequence encoding the subject protein. The subject protein encompasses synthetic polypeptides, e.g., a subject synthetic polypeptide is synthesized chemically in a laboratory (e.g., by cell-free chemical synthesis). Methods of productions are described in more detail below.

Nucleic Acid and Protein Sequences

The subject polypeptide may be generated using recombinant techniques to manipulate nucleic acids of different FAM3C known in the art to provide constructs encoding a protein of interest. It will be appreciated that, provided an amino acid sequence, the ordinarily skilled artisan will immediately recognize a variety of different nucleic acids encoding such amino acid sequence in view of the knowledge of the genetic code.

For production of subject protein derived from naturally-occurring polypeptides, it is noted that nucleic acids encoding a variety of different FAM3C polypeptides are known and available in the art. Nucleic acid (and amino acid sequences) for various FAM3C are also provided in GenBank as accession nos.: 1) *Homo sapiens*: amino acid sequence NP_055703.1; nucleotide sequence: NM_014888.2; 2) *Mus musculus*: amino acid sequence NP_613053.3; nucleotide sequence NM_138587.4; 3) *Rattus norvegicus*: amino acid sequence NP_942066.1; nucleotide sequence NM_198771.1; 4) *Bos taurus*: amino acid sequence NP_001092617; nucleotide sequence NM_001099147. Exemplary amino acid sequences are depicted in FIG. 11. Several sequences and further information on the nucleic acid and protein sequences can also be found in the Example section below.

It will be appreciated that the nucleotide sequences encoding the protein may be modified so as to optimize the codon usage to facilitate expression in a host cell of interest (e.g., *Escherichia. coli*, and the like). Methods for production of codon optimized sequences are known in the art.

Protein Modifications

The proteins used in the present disclosure can be provided as proteins that are modified relative to the naturally-occurring protein. Purposes of the modifications may be to increase a property desirable in a protein formulated for therapy (e.g. serum half-life), to raise antibody for use in detection assays, and/or for protein purification, and the like.

One way to modify a subject protein is to conjugate (e.g. link) one or more additional elements at the N- and/or C-terminus of the protein, such as another protein (e.g. having an amino acid sequence heterologous to the subject protein) and/or a carrier molecule. Thus, an exemplary protein can be provided as fusion proteins with a polypeptide(s) derived from a FAM3C polypeptide.

Conjugate modifications to proteins may result in a protein that retains the desired activity, while exploiting properties of the second molecule of the conjugate to impart and/or enhances certain properties (e.g. desirable for therapeutic uses). For example, the polypeptide may be conjugated to a molecule, e.g., to facilitate solubility, storage, half-life, reduction in immunogenicity, controlled release in tissue or other bodily location (e.g., blood or other particular organs, etc.).

Other features of a conjugated protein may include one where the conjugate reduces toxicity relative to unconjugated protein. Another feature is that the conjugate may target a type of cell or organ more efficiently than an unconjugated material. The protein can optionally have attached a drug to further counter the causes or effects associated with disorders of glucose metabolism (e.g., drug for high cholesterol), and/or can optionally be modified to provide for improved pharmacokinetic profile (e.g., by PEGylation, hyperglycosylation, and the like).

Modifications that can enhance serum half-life of the subject proteins are of interest. A subject protein may be "PEGylated", as containing one or more poly(ethylene glycol) (PEG) moieties. Methods and reagents suitable for PEGylation of a protein are well known in the art and may be found in U.S. Pat. No. 5,849,860, disclosure of which is incorporated herein by reference. PEG suitable for conjugation to a protein is generally soluble in water at room temperature, and has the general formula $R(O-CH_2-CH_2)_nO-R$, where R is hydrogen or a protective group such as an alkyl or an alkanol group, and where n is an integer from 1 to 1000. Where R is a protective group, it generally has from 1 to 8 carbons.

The PEG conjugated to the subject protein can be linear. The PEG conjugated to the subject protein may also be branched. Branched PEG derivatives such as those described in U.S. Pat. No. 5,643,575, "star-PEG's" and multi-armed PEG's such as those described in Shearwater Polymers, Inc. catalog "Polyethylene Glycol Derivatives 1997-1998." Star PEGs are described in the art including, e.g., in U.S. Pat. No. 6,046,305.

Where the proteins are to be incorporated into a liposome, carbohydrate, lipid moiety, including N-fatty acyl groups such as N-lauroyl, N-oleoyl, fatty amines such as dodecyl amine, oleoyl amine, and the like (e.g., see U.S. Pat. No. 6,638,513) may also be used to modify the subject proteins.

Where the subject proteins are used to raise antibodies specific for the subject protein, elements that may be conjugated include large, slowly metabolized macromolecules such as: proteins; polysaccharides, such as sepharose, agarose, cellulose, cellulose beads and the like; polymeric amino acids such as polyglutamic acid, polylysine, and the like; amino acid copolymers; inactivated virus particles; inactivated bacterial toxins such as toxoid from diphtheria, tetanus, cholera, leukotoxin molecules; liposomes; inactivated bacteria; dendritic cells; and the like.

Additional suitable carriers used in eliciting antibodies are well known in the art, and include, e.g., thyroglobulin, albumins such as human serum albumin, tetanus toxoid; Diphtheria toxoid; polyamino acids such as poly(D-lysine:D-glutamic acid); VP6 polypeptides of rotaviruses; influenza virus hemagglutinin, influenza virus nucleoprotein; hepatitis B virus core protein, hepatitis B virus surface antigen; purified protein derivative (PPD) of tuberculin from *Mycobacterium tuberculosis*; inactivated *Pseudomonas aeruginosa* exotoxin A (toxin A); Keyhole Limpet Hemocyanin (KLH); filamentous hemagglutinin (FHA) of *Bordetella pertussis*; T helper cell (Th) epitopes of tetanus toxoid (TT) and *Bacillus Calmette-Guerin* (BCG) cell wall; recombinant 10 kDa, 19 kDa and 30-32 kDa proteins from *M. leprae* or from *M. tuberculosis*, or any combination of these proteins; and the like. See, e.g., U.S. Pat. No. 6,447,778 for a discussion of carriers, and for methods of conjugating peptides to carriers.

Where the subject protein is to be isolated from a source, the subject protein can be conjugated to moieties the facilitate purification, such as members of specific binding pairs, e.g., biotin (member of biotin-avidin specific binding pair), an antibody, a lectin, and the like. A subject protein can also be bound to (e.g., immobilized onto) a solid support, including, but not limited to, polystyrene plates or beads, magnetic beads, test strips, membranes, and the like.

Where the proteins are to be detected in an assay, the subject proteins may also contain a detectable label, e.g., a radioisotope (e.g., $^{125}I$; $^{35}S$, and the like), an enzyme which generates a detectable product (e.g., luciferase, β-galactosidase, horse radish peroxidase, alkaline phosphatase, and the like), a fluorescent protein, a chromogenic protein, dye (e.g., fluorescein isothiocyanate, rhodamine, phycoerythrin, and the like); fluorescence emitting metals, e.g., $^{152}Eu$, or others of the lanthanide series, attached to the protein through metal chelating groups such as EDTA; chemiluminescent compounds, e.g., luminol, isoluminol, acridinium salts, and the like; bioluminescent compounds, e.g., luciferin; fluorescent proteins; and the like. Indirect labels include antibodies specific for a subject protein, wherein the antibody may be detected via a secondary antibody; and members of specific binding pairs, e.g., biotin-avidin, and the like.

Any of the above elements that are used to modify the subject proteins may be linked to the polypeptide via a linker, e.g. a flexible linker. Where a subject protein is a fusion protein comprising a FAM3C polypeptide and a heterologous fusion partner polypeptide, a subject fusion protein can have a total length that is equal to the sum of the FAM3C polypeptide and the heterologous fusion partner polypeptide.

Linkers suitable for use in modifying the proteins of the present disclosure include "flexible linkers". If present, the linker molecules are generally of sufficient length to permit the protein and a linked carrier to allow some flexible movement between the protein and the carrier. The linker molecules are generally about 6-50 atoms long. The linker molecules may also be, for example, aryl acetylene, ethylene glycol oligomers containing 2-10 monomer units, diamines, diacids, amino acids, or combinations thereof. Other linker molecules which can bind to polypeptides may be used in light of this disclosure.

Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids.

Exemplary flexible linkers include glycine polymers $(G)_n$, glycine-serine polymers (including, for example, $(GS)_n$, $GSGGS_n$ (SEQ ID NO: 1) and $GGGS_n$ (SEQ ID NO: 2), where n is an integer of at least one), glycine-alanine polymers, alanine-serine polymers, and other flexible linkers known in the art. Glycine and glycine-serine polymers are of interest since both of these amino acids are relatively unstructured, and therefore may serve as a neutral tether between components. Glycine polymers are of particular interest since glycine accesses significantly more phi-psi space than even alanine, and is much less restricted than residues with longer side chains (see Scheraga, Rev. Computational Chem. 11173-142 (1992)). Exemplary flexible linkers include, but are not limited GGSG (SEQ ID NO:3), GGSGG (SEQ ID NO:4), GSGSG (SEQ ID NO: 5), GSGGG (SEQ ID NO: 6), GGGSG (SEQ ID NO: 7), GSSSG (SEQ ID NO: 8), and the like. The ordinarily skilled artisan will recognize that design of a peptide conjugated to any elements described above can include linkers that are all or partially flexible, such that the linker can include a flexible linker as well as one or more portions that confer less flexible structure.

Methods of Production

The proteins of the present disclosure can be produced by any suitable method, including recombinant and non-recombinant methods (e.g., chemical synthesis). Where a polypeptide is chemically synthesized, the synthesis may proceed via liquid-phase or solid-phase. Solid-phase synthesis (SPPS) allows the incorporation of unnatural amino acids and/or peptide/protein backbone modification. Various forms of SPPS, such as Fmoc and Boc, are available for synthesizing peptides of the present invention. Details of the chemical synthesis are known in the art (e.g. Ganesan A. 2006 *Mini Rev. Med Chem.* 6:3-10 and Camarero J A et al. 2005 *Protein Pept Lett.* 12:723-8). Briefly, small insoluble, porous beads are treated with functional units on which peptide chains are built. After repeated cycling of coupling/deprotection, the free N-terminal amine of a solid-phase attached is coupled to a single N-protected amino acid unit. This unit is then deprotected, revealing a new N-terminal amine to which a further amino acid may be attached. The peptide remains immobilized on the solid-phase and undergoes a filtration process before being cleaved off.

Where the protein is produced using recombinant techniques, the proteins may be produced as an intracellular protein or as a secreted protein, using any suitable construct and any suitable host cell, which can be a prokaryotic or eukaryotic cell, such as a bacterial (e.g. *E. coli*) or a yeast host cell, respectively.

Other examples of eukaryotic cells that may be used as host cells include insect cells, mammalian cells, and/or plant cells. Where mammalian host cells are used, the cells may include one or more of the following: human cells (e.g. HeLa, 293, H9 and Jurkat cells); mouse cells (e.g., NIH3T3, L cells, and C127 cells); primate cells (e.g. Cos 1, Cos 7 and CV1) and hamster cells (e.g., Chinese hamster ovary (CHO) cells).

A wide range of host-vector systems suitable for the expression of the subject protein may be employed according standard procedures known in the art. See for example, Sambrook et al. 1989 *Current Protocols in Molecular Biology* Cold Spring Harbor Press, New York and Ausubel et al. 1995 *Current Protocols in Molecular Biology*, Eds. Wiley and Sons.

Methods for introduction of genetic material into host cells include, for example, transformation, electroporation, conjugation, calcium phosphate methods and the like. The method for transfer can be selected so as to provide for stable expression of the introduced FAM3C-encoding nucleic acid. The polypeptide-encoding nucleic acid can be provided as an inheritable episomal element (e.g., plasmid) or can be genomically integrated. A variety of appropriate vectors for use in production of a polypeptide of interest are available commercially.

Vectors can provide for extrachromosomal maintenance in a host cell or can provide for integration into the host cell genome. The expression vector provides transcriptional and translational regulatory sequences, and may provide for inducible or constitutive expression, where the coding region is operably linked under the transcriptional control of the transcriptional initiation region, and a transcriptional and translational termination region. In general, the transcriptional and translational regulatory sequences may include, but are not limited to, promoter sequences, ribosomal binding sites, transcriptional start and stop sequences, translational start and stop sequences, and enhancer or activator sequences. Promoters can be either constitutive or inducible, and can be a strong constitutive promoter (e.g., T7, and the like).

Expression constructs generally have convenient restriction sites located near the promoter sequence to provide for the insertion of nucleic acid sequences encoding proteins of interest. A selectable marker operative in the expression host may be present to facilitate selection of cells containing the vector. In addition, the expression construct may include additional elements. For example, the expression vector may have one or two replication systems, thus allowing it to be maintained in organisms, for example in mammalian or insect cells for expression and in a prokaryotic host for cloning and amplification. In addition the expression construct may contain a selectable marker gene to allow the selection of transformed host cells. Selectable genes are well known in the art and will vary with the host cell used.

Isolation and purification of a protein can be accomplished according to methods known in the art. For example, a protein can be isolated from a lysate of cells genetically modified to express the protein constitutively and/or upon induction, or from a synthetic reaction mixture, by immunoaffinity purification, which generally involves contacting the sample with an anti-protein antibody, washing to remove non-specifically bound material, and eluting the specifically bound protein. The isolated protein can be further purified by dialysis and other methods normally employed in protein purification methods. In one embodiment, the protein may be isolated using metal chelate chromatography methods. Protein of the present disclosure may contain modifications to facilitate isolation, as discussed above.

The subject proteins may be prepared in substantially pure or isolated form (e.g., free from other polypeptides). The protein can present in a composition that is enriched for the polypeptide relative to other components that may be present (e.g., other polypeptides or other host cell components). Purified protein may be provided such that the protein is present in a composition that is substantially free of other expressed proteins, e.g., less than 90%, usually less than 60% and more usually less than 50% of the composition is made up of other expressed proteins.

Compositions

The present disclosure provides compositions comprising a subject protein, which may be administered to a subject in need of restoring glucose homeostasis.

A subject protein composition can comprise, in addition to a subject protein, one or more of: a salt, e.g., NaCl, MgCl, KCl, MgSO$_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a protease inhibitor; glycerol; and the like.

Compositions comprising a subject protein may include a buffer, which is selected according to the desired use of the protein, and may also include other substances appropriate to the intended use. Those skilled in the art can readily select an appropriate buffer, a wide variety of which are known in the art, suitable for an intended use.

The composition may comprise a pharmaceutically acceptable excipient, a variety of which are known in the art and need not be discussed in detail herein. Pharmaceutically acceptable excipients have been amply described in a variety of publications, including, for example, "Remington: The Science and Practice of Pharmacy", 19$^{th}$ Ed. (1995), or latest edition, Mack Publishing Co; A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds 7$^{th}$ ed., Lippincott, Williams, & Wilkins; and Handbook of Pharmaceutical Excipients (2000) A. H. Kibbe et al., eds., 3$^{rd}$ ed. Amer. Pharmaceutical Assoc.

A subject pharmaceutical composition can comprise a FAM3C polypeptide (e.g., a purified FAM3C polypeptide), and a pharmaceutically acceptable excipient. In some cases, a subject pharmaceutical composition will be suitable for injection into a subject, e.g., will be sterile. For example, in some embodiments, a subject pharmaceutical composition will be suitable for injection into a human subject, e.g., where the composition is sterile and is free of detectable pyrogens and/or other toxins.

The protein compositions may comprise other components, such as pharmaceutical grades of mannitol, lactose, starch, magnesium stearate, sodium saccharin, talcum, cellulose, glucose, sucrose, magnesium, carbonate, and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate, hydrochloride, sulfate salts, solvates (e.g., mixed ionic salts, water, organics), hydrates (e.g., water), and the like.

For example, compositions may include aqueous solution, powder form, granules, tablets, pills, suppositories, capsules, suspensions, sprays, and the like. The composition may be formulated according to the different routes of administration described later below.

Where the protein is administered as an injectable (e.g. subcutaneously, intraperitoneally, and/or intravenous) directly into a tissue, a formulation can be provided as a ready-to-use dosage form, or as non-aqueous form (e.g. a reconstitutable storage-stable powder) or aqueous form, such as liquid composed of pharmaceutically acceptable carriers and excipients. The protein-containing formulations may also be provided so as to enhance serum half-life of the subject protein following administration. For example, the protein may be provided in a liposome formulation, prepared as a colloid, or other conventional techniques for extending serum half-life. A variety of methods are available for preparing liposomes, as described in, e.g., Szoka et al. 1980 *Ann. Rev. Biophys. Bioeng.* 9:467, U.S. Pat. Nos. 4,235,871, 4,501,728 and 4,837,028. The preparations may also be provided in controlled release or slow-release forms.

Other examples of formulations suitable for parenteral administration include isotonic sterile injection solutions, anti-oxidants, bacteriostats, and solutes that render the formulation isotonic with the blood of the intended recipient, suspending agents, solubilizers, thickening agents, stabilizers, and preservatives. For example, a subject pharmaceutical composition can be present in a container, e.g., a sterile container, such as a syringe. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

The concentration of the subject proteins in a formulation can vary widely (e.g., from less than about 0.1%, usually at or at least about 2% to as much as 20% to 50% or more by weight) and will usually be selected primarily based on fluid volumes, viscosities, and patient-based factors in accordance with the particular mode of administration selected and the patient's needs.

Patient Populations

The present disclosure provides a method to treat a patient suffering from hyperglycemia, hyperinsulinemia, and/or glucose intolerance. Such conditions are also commonly associated with many other glucose metabolism disorders. As such, patients of glucose metabolism disorders can be candidates for therapy according to the subject methods.

The phrase "glucose metabolism disorder" encompasses any disorder characterized by a clinical symptom or a combination of clinical symptoms that are associated with an elevated level of glucose and/or an elevated level of insulin in a subject relative to a healthy individual. Elevated levels of glucose and/or insulin may be manifested in the following disorders and/or conditions: type II diabetes (e.g. insulin-resistance diabetes), gestational diabetes, insulin resistance, impaired glucose tolerance, hyperinsulinemia, impaired glucose metabolism, pre-diabetes, metabolic disorders (such as metabolic syndrome which is also referred to as syndrome X), obesity, obesity-related disorder.

An example of a suitable patient may be one who is hyperglycemic and/or hyperinsulinemic and who is also diagnosed with diabetes mellitus (e.g. Type II diabetes). "Diabetes" refers to a progressive disease of carbohydrate metabolism involving inadequate production or utilization of insulin and is characterized by hyperglycemia and glycosuria.

"Hyperglycemia", as used herein, is a condition in which an elevated amount of glucose circulates in the blood plasma relative to a healthy individual and can be diagnosed using methods known in the art. For example, hyperglycemia can be diagnosed as having a fasting blood glucose level between 5.6 to 7 mM (pre-diabetes), or greater than 7 mM (diabetes).

"Hyperinsulinemia", as used herein, is a condition in which there are elevated levels of circulating insulin while blood glucose levels may either be elevated or remain normal. Hyperinsulininemia can be caused by insulin resistance which is associated with dyslipidemia such as high trglycerides, high cholesterol, high LDL and low HDL, high uric acids, polycystic ovary syndrome, type II diabetes and obesity. Hyperinsulinemia can be diagnosed as having a plasma insulin level higher than about 2 µU/mL.

A patient having any of the above disorders may be a suitable candidate in need of a therapy in accordance with the present method so as to receive treatment for hyperglycemia, hyperinsulinemia, and/or glucose intolerance. Administering the subject protein in such an individual can restore glucose homeostasis and may also decrease one or more of symptoms associated with the disorder.

Candidates for treatment using the subject method may be determined using diagnostic methods known in the art, e.g. by assaying plasma glucose and/or insulin levels. Candidates for treatment include those who have exhibited or are exhibiting higher than normal levels of plasma glucose/insulin. Such patients include patients who have a fasting blood glucose concentration (where the test is done after 8 to 10 hour fast) of higher than about 100 mg/dL, e.g., higher than about 110 mg/dL, higher than about 120 mg/dL, about 150 mg/dL up to about 200 mg/dL or more. Individuals suitable to be treated also include those who have a 2 hour postprandial blood glucose concentration or a concentration after a glucose tolerance test (e.g. 2 hours after ingestion of a glucose-rich drink), in which the concentration is higher than about 140 mg/dL, e.g., higher than about 150 mg/dL up to 200 mg/dL or more. Glucose concentration may also be presented in the units of mmol/L, which can be acquired by dividing mg/dL by a factor of 18.

Methods

The subject method involves administering the subject proteins in a subject who has hyperglycemia, hyperinsulinemia, and/or glucose intolerance. The methods of the present disclosure include administering FAM3C (polypeptide or nucleic acid) in the context of a variety of conditions including glucose metabolism disorders, including the examples above (in both prevention and post-diagnosis therapy).

Subjects having, suspected of having, or at risk of developing a glucose metabolism disorder are contemplated for therapy and diagnosis described herein.

By "treatment" it is meant that at least an amelioration of the symptoms associated with the condition afflicting the host is achieved, where amelioration refers to at least a reduction in the magnitude of a parameter, e.g. symptom, associated with the condition being treated. As such, treatment includes situations where the condition, or at least symptoms associated therewith, are reduced or avoided. Thus treatment includes: (i) prevention, that is, reducing the risk of development of clinical symptoms, including causing the clinical symptoms not to develop, e.g., preventing disease progression to a harmful or otherwise undesired state; (ii) inhibition, that is, arresting the development or further development of clinical symptoms, e.g., mitigating or completely inhibiting an active disease (e.g., so as to decrease level of insulin and/or glucose in the bloodstream, to increase glucose tolerance so as to minimize fluctuation of glucose levels, and/or so as to protect against diseases caused by disruption of glucose homeostasis).

In the methods of the present disclosure, protein compositions described herein can be administered to a subject (e.g. a human patient) to, for example, achieve and/or maintain glucose homeostasis, e.g., to reduce glucose level in the bloodstream and/or to reduce insulin level to a range found in a healthy individual. Subjects for treatment include those having a glucose metabolism disorder as described herein. For example, protein composition finds use in facilitating glucose homeostasis in subjects with a glucose metabolism disorder resulting from obesity.

The methods relating to disorders of the glucose metabolism contemplated herein include, for example, use of protein described above for therapy alone or in combination with other types of therapy. The method involves administering to a subject the subject protein (e.g. subcutaneously or intravenously). As noted above, the methods are useful in the context of treating or preventing a wide variety of disorders related to glucose metabolism.

Routes of Administration

In practicing the methods, routes of administration (path by which a subject protein is brought into a subject) may vary. A subject protein above can be delivered by a route that provides for delivery of the protein to the bloodstream (e.g., by parenteral administration, such as intravenous administration, intramuscular administration, and/or subcutaneous administration). Injection can be used to accomplish parenteral administration.

Combination Therapy

Any of a wide variety of therapies directed to regulating glucose metabolism, and any glucose metabolism disorders, and/or obesity, for example, can be combined in a composition or therapeutic method with the subject proteins. The subject proteins can also be administered in combination with a modified diet and/or exercise regiment to promote weight loss.

"Combination" as used herein is meant to include therapies that can be administered separately, e.g. formulated separately for separate administration (e.g., as may be provided in a kit), or undertaken as a separate regime (as in exercise and diet modifications), as well as for administration in a single formulation (i.e., "co-formulated"). Examples of agents that may be provided in a combination therapy include those that are normally administered to subjects suffering from symptoms of hyperglycemia, hyperinsulinemia, glucose intolerance, and disorders associated those conditions. Examples of agents that may be provided in a combination therapy include those that promote weight loss.

Where the subject protein is administered in combination with one or more other therapies, the combination can be administered anywhere from simultaneously to up to 5 hours or more, e.g., 10 hours, 15 hours, 20 hours or more, prior to or after administration of a subject protein. In certain embodiments, a subject protein and other therapeutic intervention are administered or applied sequentially, e.g., where a subject protein is administered before or after another therapeutic treatment. In yet other embodiments, a subject protein and other therapy are administered simultaneously, e.g., where a subject protein and a second therapy are administered at the same time, e.g., when the second therapy is a drug it can be administered along with a subject protein as two separate formulations or combined into a single composition that is administered to the subject. Regardless of whether administered sequentially or simultaneously, as illustrated above, the treatments are considered to be administered together or in combination for purposes of the present disclosure.

Additional standard therapeutics for glucose metabolism disorders that may or may not be administered in conjunction with a subject protein, include but not limited to any of the combination therapies described above, hormonal therapy, immunotherapy, chemotherapeutic agents and surgery.

Dosages

In the methods, a therapeutically effective amount of a subject protein is administered to a subject in need thereof. For example, a subject protein causes the level of plasma glucose and/or insulin to return to a normal level relative to a healthy individual when the subject protein is delivered to the bloodstream in an effective amount to a patient who previously did not have a normal level of glucose/insulin relative to a healthy individual prior to being treated. The amount administered varies depending upon the goal of the administration, the health and physical condition of the individual to be treated, age, the degree of resolution desired, the formulation of a subject protein, the activity of the subject proteins employed, the treating clinician's assessment of the medical situation, the condition of the subject, and the body weight of the subject, as well as the severity of the dysregulation of glucose/insulin and the stage of the disease, and other relevant factors. The size of the dose will also be determined by the existence, nature, and extent of any adverse side-effects that might accompany the administration of a particular protein.

It is expected that the amount will fall in a relatively broad range that can be determined through routine trials. For example, the amount of subject protein employed to restore glucose homeostasis is not more than about the amount that could otherwise be irreversibly toxic to the subject (i.e., maximum tolerated dose). In other cases, the amount is around or even well below the toxic threshold, but still in an effective concentration range, or even as low as threshold dose.

Also, suitable doses and dosage regimens can be determined by comparisons to indicators of glucose metabolism. Such dosages include dosages which result in the stabilized levels of glucose and insulin, for example, comparable to a healthy individual, without significant side effects. Dosage treatment may be a single dose schedule or a multiple dose schedule (e.g., including ramp and maintenance doses). As indicated below, a subject composition may be administered in conjunction with other agents, and thus doses and regiments can vary in this context as well to suit the needs of the subject.

Individual doses are typically not less than an amount required to produce a measurable effect on the subject, and may be determined based on the pharmacokinetics and pharmacology for absorption, distribution, metabolism, and excretion ("ADME") of the subject protein or its by-products, and thus based on the disposition of the composition within the subject. This includes consideration of the route of administration as well as dosage amount, which can be adjusted for enteral (applied via digestive tract for systemic or local effects when retained in part of the digestive tract) or parenteral (applied by routes other than the digestive tract for systemic or local effects) applications. For instance, administration of a subject protein is typically via injection and often intravenous, intramuscular, or a combination thereof.

By "therapeutically effective amount" is meant that the administration of that amount to an individual, either in a single dose, as part of a series of the same or different protein compositions, is effective to help restore homeostasis of glucose metabolism as assessed by glucose and/or insulin levels in a subject. As noted above, the therapeutically effective amount can be adjusted in connection with dosing regimen and diagnostic analysis of the subject's condition (e.g., monitoring for the levels of glucose and/or insulin in the plasma) and the like.

As an example, the effective amount of a dose or dosing regimen can be gauged from the $ED_{50}$ of a protein for inducing an action that leads to clearing glucose from the bloodstream or lowering of insulin levels. By "$ED_{50}$" (effective dosage) is the intended dosage which induces a response halfway between the baseline and maximum after some specified exposure time. The $ED_{50}$ of a graded dose response curve therefore represents the concentration of a subject protein where 50% of its maximal effect is observed. $ED_{50}$ may be determined by in vivo studies (e.g. animal models) using methods known in the art.

An effective amount may not be more than 100× the calculated $ED_{50}$. For instance, the amount of protein that is administered is less than about 100×, less than about 50×, less than about 40×, 35×, 30×, or 25× and many embodiments less than about 20×, less than about 15× and even less than about 10×, 9×, 8×, 7×, 6×, 5×, 4×, 3×, 2× or 1× than the calculated $ED_{50}$. In one embodiment, the effective amount is about 1× to 30× of the calculated $ED_{50}$, and sometimes about 1× to 20×, or about 1× to 10× of the calculated $ED_{50}$. In other embodiments, the effective amount is the same as the calculated $ED_{50}$, and in certain embodiments the effective amount is an amount that is more than the calculated $ED_{50}$.

An effective amount of a protein may also an amount that is effective, when administered in one or more doses, to reduce in an individual a level of plasma glucose and/or plasma insulin that is elevated relative to that of a healthy individual by at least about 10%, at least about 20%, at least about 25%, at least about 30%, at least about 40%, at least about 50%, at least about 60%, at least about 70%, at least about 80%, or more than 80%, compared to an elevated level of plasma glucose/insulin in the individual not treated with the protein.

Further examples of dose per administration may be at less than 10 µg, less than 2 µg, or less than 1 µg. Dose per administration may also be more than 50 µg, more 100 µg, more than 300 µg to 600 µg or more. An example of a range of dosage per weight is about 0.1 µg/kg to about 1 µg/kg, up to about 1 mg/kg or more. Effective amounts and dosage regimen can readily be determined empirically from assays, from safety and escalation and dose range trials, individual clinician-patient relationships, as well as in vitro and in vivo assays known in the art.

The term "unit dosage form," as used herein, refers to physically discrete units suitable as unitary dosages for human and animal subjects, each unit containing a predetermined quantity of proteins of the present disclosure calculated in an amount sufficient to produce the desired effect in association with a pharmaceutically acceptable diluent, carrier or vehicle. The specifications for the novel unit dosage forms depend on the particular protein employed and the effect to be achieved, and the pharmacodynamics associated with each protein in the host.

Kits

Also provided by the present disclosure are kits for using the compositions disclosed herein and for practicing the methods, as described above. The kits may be provided for administration of the subject protein in a subject in need of restoring glucose homeostasis. The kit can include one or more of the proteins disclosed herein, which may be provided in a sterile container, and can be provided in formulation with a suitable a pharmaceutically acceptable excipient for administration to a subject. The proteins can be provided with a formulation that is ready to be used as it is or can be reconstituted to have the desired concentrations. Where the proteins are provided to be reconstituted by a user, the kit may also provide buffers, pharmaceutically acceptable excipient, and the like, packaged separately from the subject protein. The proteins of the present kit may be formulated separately or in combination with other drugs. Kits can include, for example: 1) a first container (e.g., a sterile container) comprising a subject pharmaceutical composition; and 2) a second container (e.g., a sterile container) comprising a second agent (e.g., a second agent that can lower blood glucose levels).

In addition to above-mentioned components, the kits can further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); nt, nucleotide(s); i.m., intramuscular(ly); i.p., intraperitoneal(ly); s.c., subcutaneous(ly); and the like.

Materials and Methods

The following methods and materials were used in the Examples below.

Animals. C57BL/6 mice were purchased from the Charles River Laboratory (Wilmington, Mass.), Mice were kept in accordance with welfare guidelines and project license restrictions under controlled light (12 hr light and 12 hr dark cycle, dark 6:30 pm-6:30 am), temperature (22±4° C.) and humidity (50%±20%) conditions. They had free access to water (autoclaved distilled water) and were fed ad libitum on a commercial diet (Harlan laboratories, Irradiated 2018 Teklad Global 18% Protein Rodent Diet) containing 17 kcal % fat, 23 kcal % protein and 60 kcal % carbohydrate. Alternatively, mice were maintained on a high-fat diet (D12492, Research Diets, New Brunswick, N.J. USA) containing 60 kcal % fat, 20 kcal % protein and 20 kcal % carbohydrate. All animal studies were approved by the NGM Institutional Animal Care and Use Committee for NGM-5-2008 entitled "Characterization Of Biologics, Compounds And Viral Vectors For Treatment Of Diabetes Using Rodent Model".

DNA and amino acid sequences.

```
cDNA of ORF encoding murine FAM3C
(GenBank Accession No. NM_138587.4)
                                          (SEQ ID NO: 9)
ATGAGGGTAGCAGGAGCTGCAAAGTTGGTAGTGGCCGTGGCAGTATTC

TTACTGACCTTCTATGTTATTTCTCAAGTATTTGAAATTAAAATGGAT

GCAAGTTTAGGAAATCTATTTGCTCGATCCGCGCTGGACTCAGCCATT

CGTTCTACGAAACCTCCGAGGTACAAGTGTGGGATCTCAAAGGCGTGC

CCAGAGAAGCATTTTGCTTTTAAGATGGCTAGTGGAGCAGCCAATGTC

GTGGGACCCAAGATCTGCCTGGAGGACAATGTTTTGATGAGTGGTGTG

AAGAATAATGTCGGAAGAGGAATCAATATTGCCTTGGTAAATGGGAAA

ACAGGGGAAGTAATAGACACCAAATTTTTTGACATGTGGGGAGGAGAT

GTGGCACCATTCATTGAGTTTTTGAAGACCATACAAGACGGAACAGTA

GTGCTAATGGCTACATACGATGATGGAGCAACCAAACTCACGGATGAG

GCACGGCGGCTCATTGCTGAACTGGGCAGCACTTCGATCACCAGTCTT

GGTTTCCGAGATAACTGGGTCTTCTGTGGTGGGAAGGGCATTAAGACA

AAGAGTCCCTTTGAACAGCACATAAAGAACAATAAGGAAACGAACAAG

TACGAGGGATGGCCTGAGGTGGTGGAGATGGAAGGATGTATCCCCCAG

AAGCAAGACTGA.

Protein sequence encoded by the cDNA
(GenBank Accession No. NP_613053.3)
                                          (SEQ ID NO: 10)
MRVAGAAKLVVAVAVFLLTFYVISQVFEIKMDASLGNLFARSALDSAI

RSTKPPRYKCGISKACPEKHFAFKMASGAANVVGPKICLEDNVLMSGV

KNNVGRGINIALVNGKTGEVIDTKFFDMWGGDVAPFIEFLKTIQDGTV

VLMATYDDGATKLTDEARRLIAELGSTSITSLGFRDNWVFCGGKGIKT

KSPFEQHIKNNKETNKYEGWPEVVEMEGCIPQKQD.
```

FAM3C ORF was amplified with polymerase chain reaction (PCR) using recombinant DNA (cDNA) prepared from mouse small intestinal tissue. PCR reagents kits with Phusion high-fidelity DNA polymerase were purchased from New England BioLabs (F-530L, Ipswich, Mass.). The following primers were used: forward PCR primer: 5' ATGAGGGTAG-CAGGAGCTGCA (SEQ ID NO: 11) and reverse PCR primer: 5' TCAGTCTTGCTTCTGGGGGAT (SEQ ID NO: 12).

PCR.

The PCR reaction were set up according to manufacturer's instruction, amplified DNA fragment was digested with restriction enzymes Spe I and Not I (the restriction sites were included in the 5' or 3' PCR primers, respectively) and was then ligated with AAV transgene vectors that had been digested with the same restriction enzymes. The vector used for expression contained a selectable marker and an expression cassette composed of a strong eukaryotic promoter 5' of a site for insertion of the cloned coding sequence, followed by a 3' untranslated region and bovine growth hormone polyadenylation tail. The expression construct is also flanked by internal terminal repeats at the 5' and 3' ends.

Production and purification of AAV. AAV 293 cells (obtained from Agilent Technologies, Santa Clara, Calif.) were cultured in Dulbeco's Modification of Eagle's Medium (DMEM, Mediatech, Inc. Manassas, Va.) supplemented with 10% fetal bovine serum and 1× antibiotic-antimycotic solution (Mediatech, Inc. Manassas, Va.). The cells were plated at 50% density on day 1 in 150 mm cell culture plates and transfected on day 2, using calcium phosphate precipitation method, the following 3 plasmids (20 µg/plate of each): AAV transgene plasmid, pHelper plasmids (Agilent Technologies) and AAV2/9 plasmid (Gao et al (2004) *J. Virol.* 78:6381). 48 hours after transfection, the cells were scraped off the plates, pelleted by centrifugation at 3000×g and resuspended in buffer containing 20 mM Tris pH 8.5, 100 mM NaCl and 1 mM $MgCl_2$. The suspension was frozen in an alcohol dry ice bath and was then thawed in 37° C. water bath. The freeze and thaw cycles were repeated for a total of three times; benzonase (Sigma-Aldrich, St. Louis, Mo.) was added to 50 units/ml; deoxycholate was added to a final concentration of 0.25%. After an incubation at 37° C. for 30 min, cell debris was pelleted by centrifugation at 5000×g for 20 min. Viral particles in the supernatant were purified using a discontinued iodixanal (Sigma-Aldrich, St. Louis, Mo.) gradient as previously described (Zolotukhin S. et al (1999) *Gene Ther* 6:973). The viral stock was concentrated using Vivaspin 20 (MW cutoff 100,000 Dalton, Sartorius Stedim Biotech, Aubagne, France) and re-suspended in phosphate-buffered saline (PBS) with 10% glycerol and stored at −80° C. To determine the viral genome copy number, 2 µl of viral stock was incubated in 6 µl of solution containing 50 units/ml benzonase, 50 mM Tris-HCl pH 7.5, 10 mM $MgCl_2$ and 10 mM $CaCl_2$ for at 37° C. for 30 minutes.

Afterwards, 15 µl of the solution containing 2 mg/ml of Proteinase K, 0.5% SDS and 25 mM EDTA were added and the mixture was incubated for additional 20 min at 55° C. to release viral DNA. Viral DNA was cleaned with mini DNeasy Kit (Qiagen, Valencia, Calif.) and eluted with 40 µl of water. Viral genome copy (GC) was determined by using quantitative PCR.

Viral stock was diluted with PBS to desirable GC/ml. 200 µl of viral working solution was delivered into mice via tail vein injection.

Blood Glucose Assay.

Blood glucose in mouse tail snip was measured using ACCU-CHEK Active test strips read by an ACCU-CHEK Active meter (Roche Diagnostics, Indianapolis, Ind.) following manufacturer's instruction.

Serum Insulin Assay.

Whole blood (about 50 µl/mouse) from mouse tail snips was collected into plain capillary tubes (BD Clay Adams SurePrep, Becton Dickinson and Co. Sparks, Md.). Serum and blood cells were separated by spinning the tubes in an Autocrit Ultra 3 (Becton Dickinson and Co. Sparks, Md.). Insulin levels in serum were determined using insulin EIA kits (80-Insums-E01, Alpco Diagnostics, Salem, N.H.) by following manufacturer's instruction.

Glucose Tolerance Test (GTT).

Mice fasted for 16 hours received glucose (1 g/kg) in PBS via intra-peritoneal injection. Blood glucose levels were determined as described above at the time points indicated.

Insulin Tolerance Test (ITT).

Mice fasted for 4 hours received 0.75 units/kg of insulin (Humulin R Eli Lilly and Co. Indianapolis, Ind.) via intra-peritoneal injection. Blood glucose was determined as described above.

Statistics.

Statistical analysis was performed with Student's t-Test with 2-tailed distribution.

Example 1

Effect of in Vivo FAM3C Expression on Blood Glucose Levels in Mice with Diet-Induced Obesity To identify secreted proteins that have an effect on glucose metabolism, selected genes were overexpressed in mice using adeno-associated virus (AAV) as the gene delivery vehicle. The anti-diabetic effects of the gene products were evaluated in diet-induced obesity (DIO) model. Eight week old male C57BL/6 mice were subjected to 60% kcal fat diet for eight weeks before they received a one-time tail vein injection of recombinant AAV (rAAV). Mice body weight, blood glucose and serum insulin were determined. Glucose tolerance and insulin tolerance tests were also performed to help assess the effect of rAAV on glucose clearance and insulin sensitivity. rAAV-mediated Fam3C expression significantly reduced blood glucose levels in DIO mice without significantly changing the body weight (FIG. 1). Results of the glucose tolerance test indicated improvement of glucose disposal in these animals.

Figure 2:
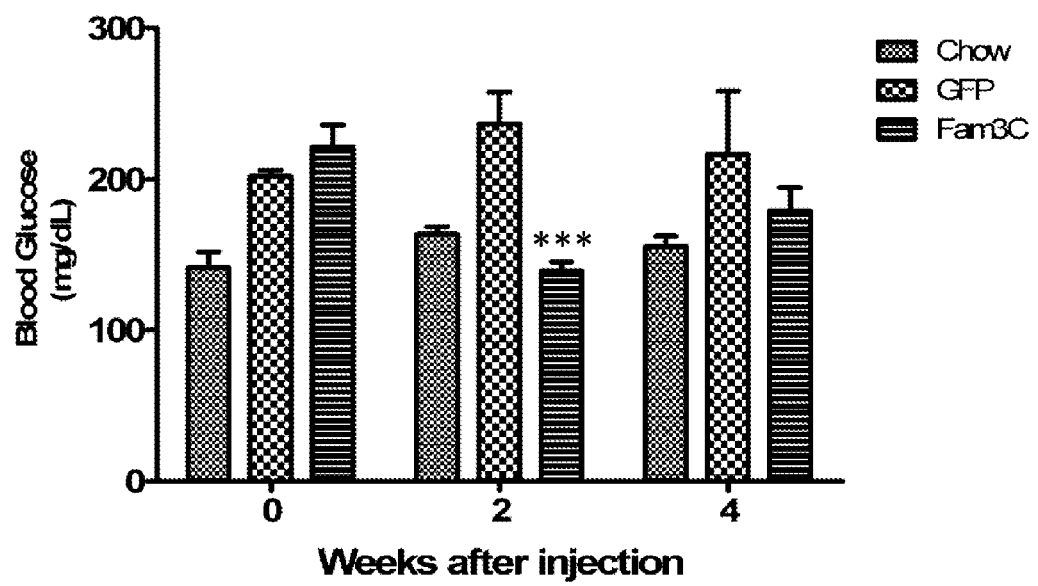
FIG. 2 shows blood glucose of mice on high fat diet that were injected with AAV expressing a protein of the present disclosure (mouse ortholog) compared to those of mice injected with a control virus and those on a lean diet (n=5 mice per group).

The ability of murine Fam3C to regulate the level of plasma glucose was tested as follows. rAAV expressing Fam3C was injected through tail vein into mice that had been on high fat diet for eight weeks. Prior to, and at two and four weeks after the injection, 4-hour fasting blood glucose levels were determined in tail blood. In FIG. 2, "Chow" refers to mice on chow diet, "GFP" to DIO mice that were injected with $1\times10^{12}$ genome copies ("1E+12" "GC") of rAAV expressing green fluorescent protein, and "Fam3C" to mice injected with 1E+12GC of rAAV expressing Fam3C (n=5 mice per group). As seen in FIG. 2, recombinant AAV expressing murine Fam3C reduced blood glucose in DIO mice to levels comparable to mice on chow diet.

Example 2

Figure 3:
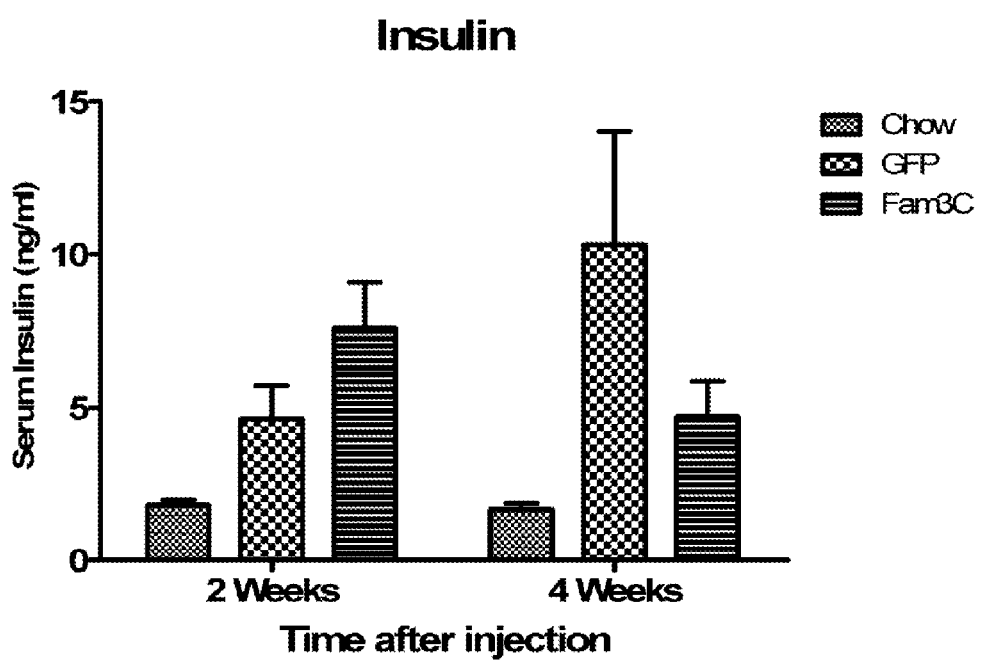
FIG. 3 shows insulin levels of mice on high fat diet that were injected with AAV expressing a protein of the present disclosure (mouse ortholog) compared to those of mice injected with a control virus and those on a lean diet (n=5 mice per group).

Effect of Murine FAM3C Expression on Serum Insulin Levels in Mice with Diet-Induced Obesity The ability of murine Fam3C to relieve hyperinsulinemia in mice with diet-induced obesity was tested. rAAV was injected through tail vein into mice that had been on high fat diet for eight weeks. At the two week and four week time points after the AAV injection, tail blood was collected from mice that had been fasting for four hours, and serum insulin were determined by enzyme-linked immunosorbent assay (ELISA). In FIG. 3, "Chow" refers to mice on chow diet; "GFP" to DIO mice that were injected with 1E+12 GC of rAAV expressing green fluorescent protein, and "Fam3C" to mice injected with 1E+12 GC of rAAV expressing Fam3C (n=5 mice per group). As seen in FIG. 3, recombinant AVV expressing murine Fam3C reduced hyperinsulinemia in DIO mice at the four week time point.

Example 3

Figure 4:
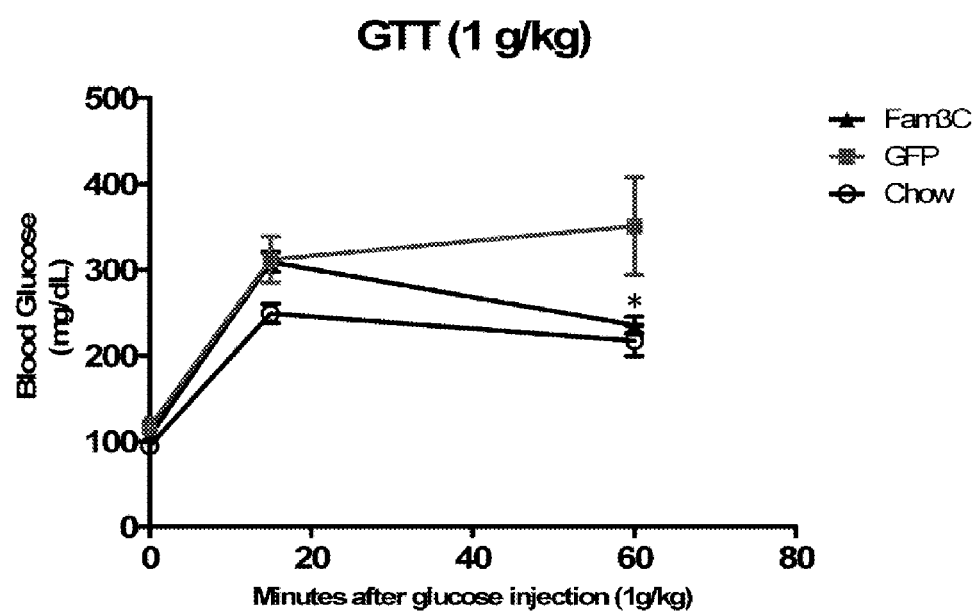
FIG. 4 shows the level of glucose in mice over a 60 minute period post injection of 1 g/kg of glucose. Glucose tolerance was monitored in mice on a high fat diet that have been injected with AVV expressing a protein provided by the present disclosure (mouse ortholog) or the control and in mice that were on a lean diet (n=5 mice per group).

Effect of Murine FAM3C Expression on Glucose Tolerance in Mice with Diet-Induced Obesity The ability of murine Fam3C to improve glucose tolerance of mice with diet-induced obesity was evaluated as follows. rAAV expressing Fam3C was injected through tail vein into mice that had been on high fat diet for eight weeks. Glucose tolerance test was performed three weeks after the AAV injection. Mice fasted overnight received 1 g/kg of glucose in PBS via intraperitoneal injection (i.p.). Blood glucose levels were determined at times indicated. In FIG. 4, "Chow" refers to mice on chow diet, "GFP" to DIO mice that were injected with 1E+12 GC of rAAV expressing green fluorescent protein, and "Fam3C" to mice injected with 1E+12 GC of rAAV expressing Fam3C (n=5 mice per group). As seen in FIG. 4, recombinant AAV expressing murine Fam3C was able to improve glucose tolerance in DIO mice.

Example 4

Figure 5:
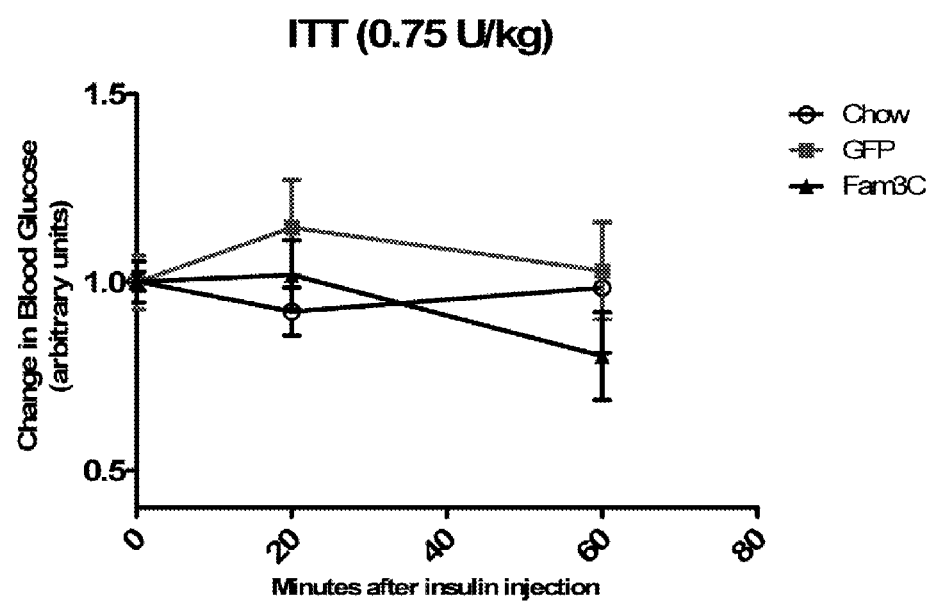
FIG. 5 shows the result of an insulin tolerance test. Glucose levels were monitored after an intraparitoneal injection of insulin (0.75 units/kg). Response to insulin was compared among DIO mice injected with AAV expressing a protein of the present disclosure (mouse ortholog) and those injected with AAV expressing the control, as well as lean mice (n=5 mice per group)

Effect of Murine FAM3C Expression on Insulin Tolerance in Mice with Diet-Induced Obesity The ability of murine Fam3C to improve insulin sensitivity of mice with diet-induced obesity was evaluated as follows. rAAV expressing Fam3C was injected through tail vein into mice that had been on high fat diet for eight weeks. An insulin tolerance test was performed five weeks after the AAV injection. Glucose levels were monitored after an intraperitoneal injection of insulin (0.75 units/kg). Response to insulin was compared among DIO mice injected with AAV expressing Fam3C, GFP and lean mice by measuring blood glucose levels at times indicated. In FIG. 5, "Chow" refers to mice on chow diet, "GFP" to DIO mice that were injected with 1E+12 GC of rAAV expressing green fluorescent protein, and "Fam3C" to mice injected with 1E+12 GC of rAAV expressing Fam3C (n=5 mice per group). As seen in FIG. 5, recombinant AAV expressing murine Fam3C was able to improve insulin sensitivity in DIO mice.

Example 5

Cloning of the Human Gene

The cloning of the human gene encoding FAM3C is carried out by using the PCR method as previously set forth for the cloning of the mouse gene. Briefly, the human FAM3C gene can be cloned out by PCR from cDNA library using the following pair of primers, and then cloned into AAV transgene vector as described above for efficacy evaluation. Forward PCR primer: 5' ATGAGGGTAGCAGGTGCTGCA (SEQ ID NO: 13). Reverse PCR primer: 5' TTAGTCTTGCT-TCTGGGGGAT (SEQ ID NO: 14).

The nucleic acid sequences, and the encoded amino acid sequence, for human FAM3C are provided below:

```
Human FAM3C ORF (GenBank Accession No. NM_014888.2)
                                           (SEQ ID NO: 15)
ATGAGGGTAGCAGGTGCTGCAAAGTTGGTGGTAGCTGTGGCAGTGTTT

TTACTGACATTTTATGTTATTTCTCAAGTATTTGAAATAAAAATGGAT

GCAAGTTTAGGAAATCTATTTGCAAGATCAGCATTGGACACAGCTGCA

CGTTCTACAAAGCCTCCCAGATATAAGTGTGGGATCTCAAAAGCTTGC

CCTGAGAAGCATTTTGCTTTTAAAATGGCAAGTGGAGCAGCCAACGTG

GTGGGACCCAAAATCTGCCTGGAAGATAATGTTTTAATGAGTGGTGTT

AAGAATAATGTTGGAAGAGGGATCAATGTTGCCTTGGCAAATGGAAAA

ACAGGAGAAGTATTAGACACTAAATATTTTGACATGTGGGGAGGAGAT

GTGGCACCATTTATTGAGTTTCTGAAGGCCATACAAGATGGAACAATA

GTTTTAATGGGAACATACGATGATGGAGCAACCAAACTCAATGATGAG

GCACGGCGGCTCATTGCTGATTTGGGGAGCACATCTATTACTAATCTT

GGTTTTAGAGACAACTGGGTCTTCTGTGGTGGGAAGGGCATTAAGACA

AAAAGCCCTTTTGAACAGCACATAAAGAACAATAAGGATACAAACAAA

TATGAAGGATGGCCTGAAGTTGTAGAAATGGAAGGATGCATCCCCCAG

AAGCAAGACTAA.

Human FAM3C 227 amino acid residues
(GenBank Accession No. NP_055703.1)
                                           (SEQ ID NO: 16)
MRVAGAAKLVVAVAVFLLTFYVISQVFEIKMDASLGNLFARSALDTAA

RSTKPPRYKCGISKACPEKHFAFKMASGAANVVGPKICLEDNVLMSGV

KNNVGRGINVALANGKTGEVLDTKYFDMWGGDVAPFIEFLKAIQDGTI

VLMGTYDDGATKLNDEARRLIADLGSTSITNLGFRDNWVFCGGKGIKT

KSPFEQHIKNNKDTNKYEGWPEVVEMEGCIPQKQD.
```

Example 6

Treatment of Mice with Diet-Induced Obesity with rAAV Expressing Human FAM3C The human gene will be cloned into AAV transgene vector. Recombinant AAV expressing the corresponding proteins will be generated as described above in Materials and Methods.

The ability of human FAM3C (hFAM3C) to regulate the level of plasma glucose can be tested as follows. rAAV is injected through tail vein into mice that have been on high fat diet for eight weeks. Two weeks after the injection, 4-hour fasting blood glucose levels are determined in tail bleed using a glucometer. Mice tested include a lean group of mice on chow diet ("Chow"), a "GFP" group of DIO mice that are injected with 1E+12 GC of rAAV expressing green fluorescent protein, and a "hFAM3C" group of DIO mice injected with 1E+12GC of rAAV expressing hFAM3C (n=5 mice per group).

The ability of hFAM3C to relieve hyperinsulinemia in mice with diet-induced obesity can also be tested. rAAV is injected through tail vein into mice that have been on high fat diet for eight weeks. Before, and at two and four weeks after the AAV injection, tail blood is collected from mice that have been fasting for four hours, and serum insulin is determined by ELISA. Groups of mice tested can include a lean group of mice on chow diet ("Chow"), a "GFP" group of DIO mice that are injected with 1E+12 GC of rAAV expressing green fluorescent protein, and a "hFAM3C" group of DIO mice injected with 1E+12 GC of rAAV expressing hFAM3C (n=5 mice per group).

The ability of hFAM3C to improve glucose tolerance of mice with diet-induced obesity can be evaluated as follows. rAAV is injected through tail vein into mice that have been on high fat diet for eight weeks. Glucose tolerance test is performed three weeks after the AAV injection. Mice fasted overnight are injected with 1 g/kg of glucose in PBS via intraperitoneal injection (i.p.). Blood glucose levels are determined at various timed intervals. Groups of mice under evaluation include a group of lean mice on chow diet ("Chow"), a "GFP" group of DIO mice that are injected with 1E+12 GC of rAAV expressing green fluorescent protein, and a "hFAM3C" group of DIO mice injected with 1E+12GC of rAAV expressing hFAM3C (n=5 mice per group).

Example 7

Expression of Recombinant Murine and Human FAM3C

For recombinant protein expression in the mammalian expression systems, the cDNA sequence encoding the murine or human FAM3C is cloned into NheI/MluI or NheI/XbaI sites of a modified pCDNA3.1 vector, so that the expressed protein is tagged with either 6× His or human Fc. After sequence confirmation, the plasmid is tested for expression and secretion by transient transfection of the plasmids into suspension-, serum-free adapted 293T, 293-F, and CHO-S cells using FreeStyle MAX transfection reagent (Invitrogen). The identity of the secreted protein is confirmed by anti-His, Anti-hFc, and/or available gene-specific antibodies. The cell line revealing the highest level of the protein secretion is then selected for large-scale transient production of the protein in spinners and/or Wave Bioreactor® System for 5-7 days. The recombinant protein in the supernatant from the transient production is purified by Ni-NTA beads or Protein A-Sepharose affinity chromatography using ÄKTAexplorer™ (GE Healthcare), and followed by other purification methods, if needed. The purified protein is then dialyzed against PBS, concentrated to ~1 mg/ml or higher concentrations, and stored at −80° C. until use.

For recombinant protein expression in the bacterial expression system, the cDNA sequence encoding the FAM3C protein is cloned into NdeI/Hind III or KpnI/Hind III sites of pET30(+) vector, so that the expressed protein is tagged with 6× His. The sequencing confirmed plasmid is transformed into BL21(DE3) cells. The protein expression is induced by adding IPTG in the culture and confirmed with anti-His or gene-specific antibodies. If the expressed protein is in the soluble fraction, it will be purified by Ni-NTA affinity chromatography followed by other purification methods if needed. If the expressed protein is in inclusion bodies, the inclusion bodies will be isolated first. The protein in the inclusion bodies is denatured using urea or other denaturing reagents, purified by Ni-NTA beads, refolded, and further purified using other methods if needed. Endotoxin level in the purified protein is then examined, and removed by different methods until the endotoxin level is within the acceptable range. The protein is then dialyzed, concentrated and stored as described above.

Example 8

Treatment of Mice with Diet-Induced Obesity with Human FAM3C Recombinant Protein The ability of murine and human FAM3C to regulate the level of plasma glucose can be tested as follows. Recombinant murine or human FAM3C protein and control protein dissolved in PBS is injected into mice on high-fat diet at 30, 10, and 3 mg/kg via IP, SC or IV once a day for two weeks. Body weight, 4-hour fasting blood glucose levels are determined one and two weeks after the initiation of injections. Glucose tolerance test is carried out performed in week 2 and serum insulin is also determined in week 2. Assays are performed as described above in Examples 1-4.

Example 9

Figure 6:
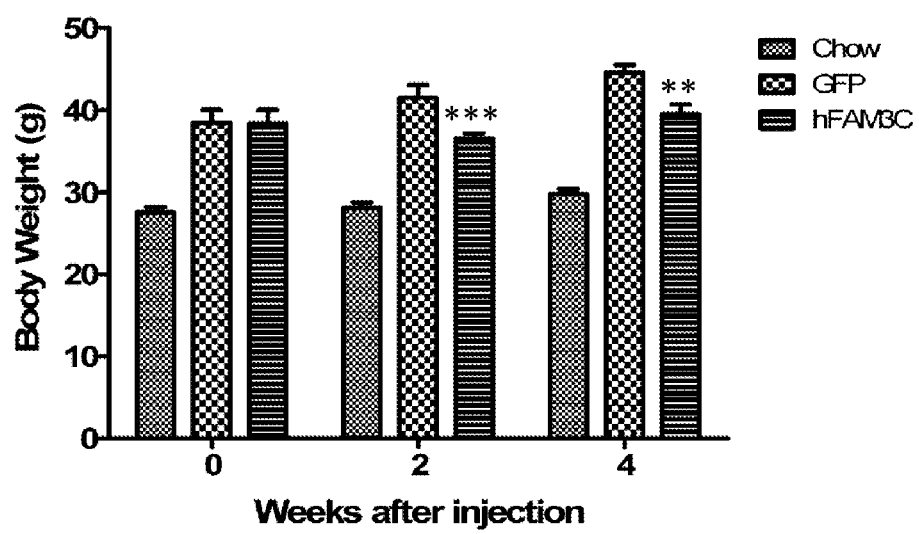
FIG. 6 shows body weight of mice on a high fat diet that were injected with AAV expressing a protein of the present disclosure (human ortholog) compared to those of mice injected with a control virus and those on a lean diet (n=5 mice per group).
Figure 7:
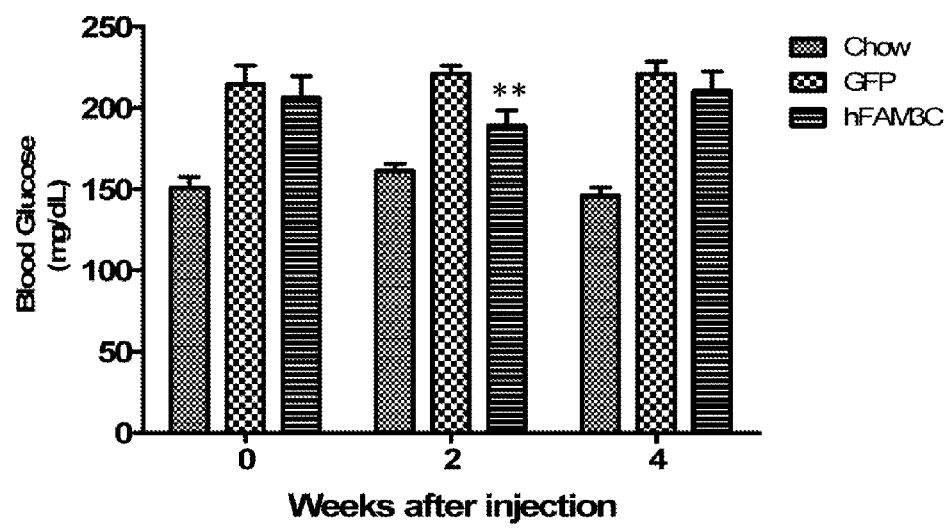
FIG. 7 shows blood glucose of mice on high fat diet that were injected with AAV expressing a protein of the present disclosure (human ortholog) compared to those of mice injected with a control virus and those on a lean diet (n=5 mice per group).
Figure 8:
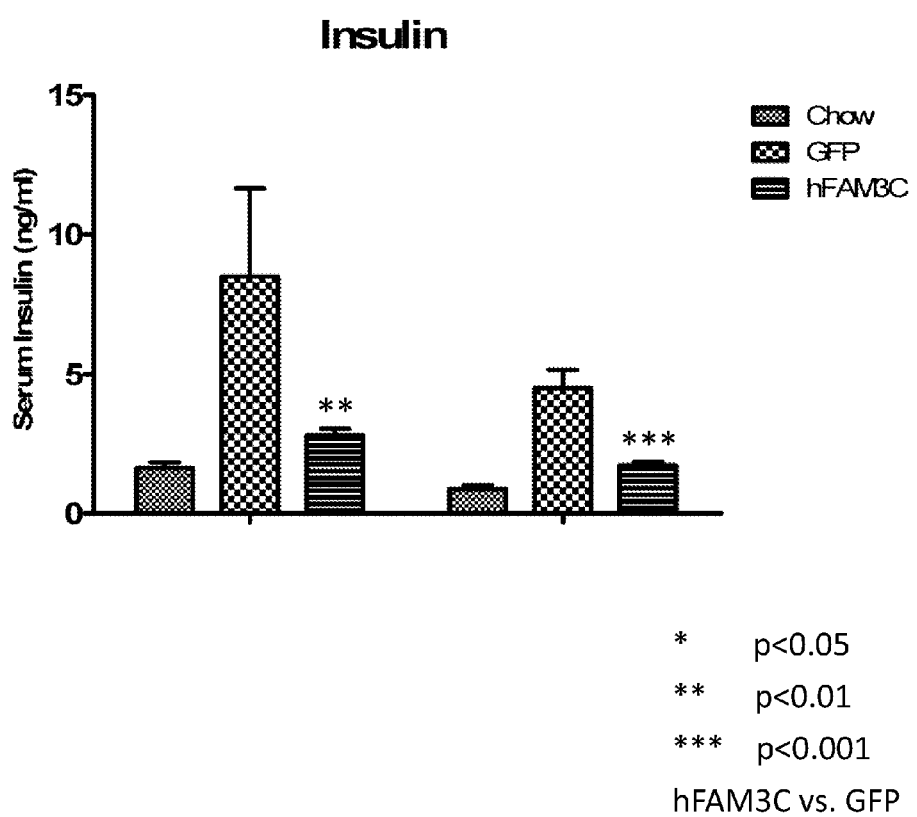
FIG. 8 shows insulin levels of mice on high fat diet that were injected with AAV expressing a protein of the present disclosure (human ortholog) compared to those of mice injected with a control virus and those on a lean diet (n=5 mice per group).
Figure 9:
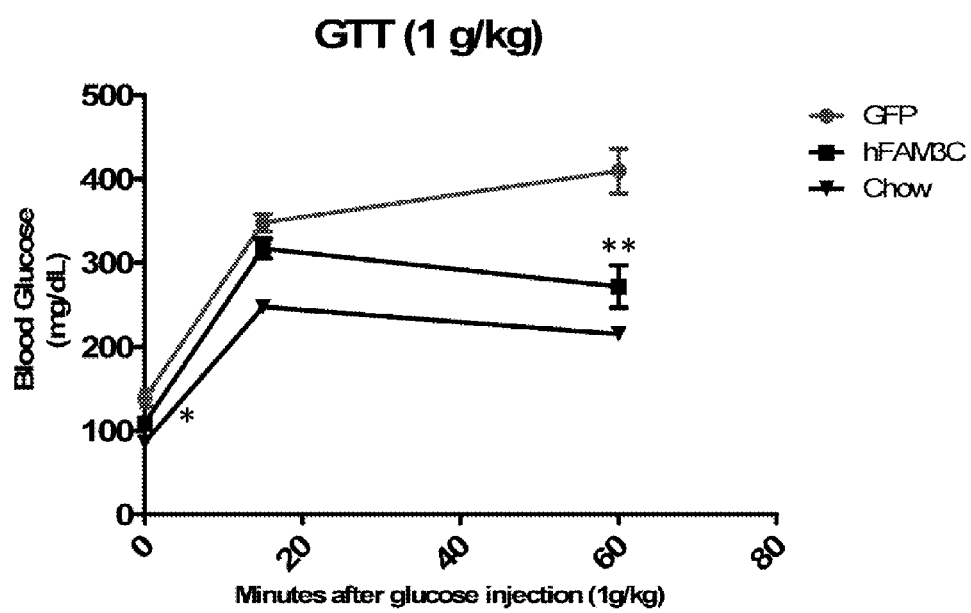
FIG. 9 shows the level of glucose in mice over a 60 minute period post injection of 1 g/kg of glucose. Glucose tolerance was monitored in mice on a high fat diet that have been injected with AVV expressing a protein provided by the present disclosure (human ortholog) compared to those of mice injected with a control virus, as well as lean mice (n=5 mice per group).
Figure 10:
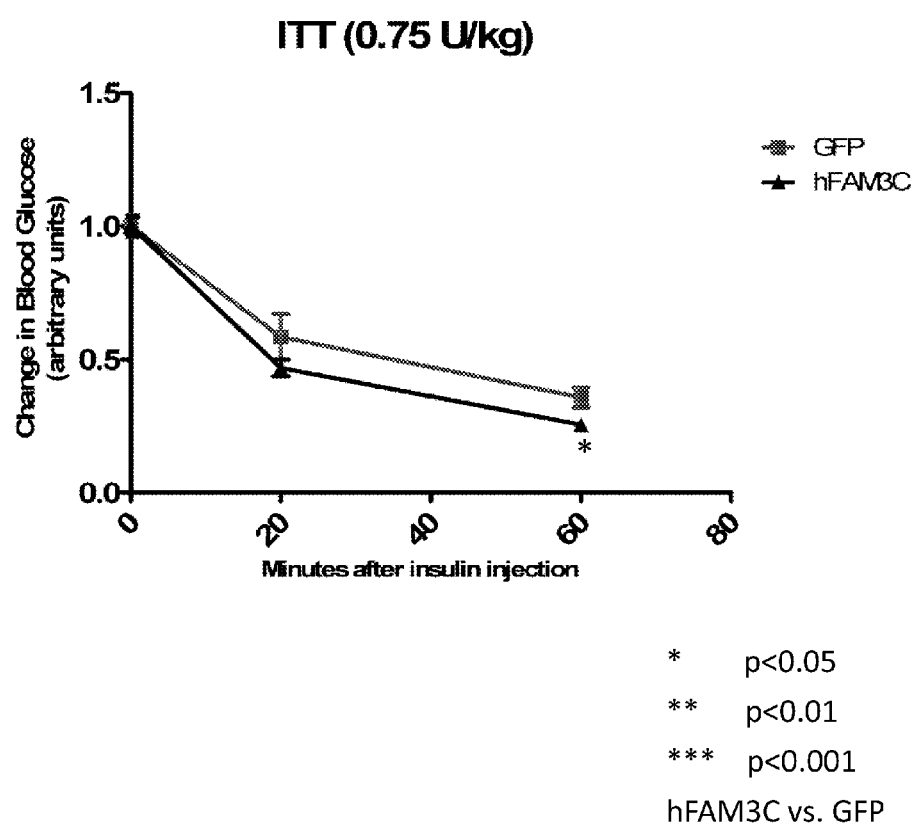
FIG. 10 shows the result of an insulin tolerance test. Glucose levels were monitored after an intraperitoneal injection of insulin (0.75 units/kg). Response to insulin was compared among diet-induced obesity (DIO) mice injected with AAV expressing a protein of the present disclosure (human ortholog) and those injected with AAV expressing the control (n=5 mice per group).

Effect of in Vivo Human FAM3C Expression on Blood Glucose Levels in Mice with Diet-Induced Obesity The anti-diabetic effect of human FAM3C was evaluated in the DIO mouse model described above. As described in Example 1, eight-week-old male C57BL/6 mice were subjected to 60% kcal fat diet for eight weeks before they received a one-time tail vein injection of rAAV comprising a nucleotide sequence encoding human FAM3C. Mice body weight, blood glucose, and serum insulin were determined. Glucose tolerance and insulin tolerance tests were also performed to help assess the effect of rAAV on glucose clearance and insulin sensitivity. rAAV-mediated human FAM3C expression significantly reduced body weight, blood glucose, and serum insulin levels in DIO mice (FIGS. 6-8). Results of the glucose and insulin tolerance tests indicated improvement of glucose disposal and insulin sensitivity in these animals (FIGS. 9-10).

The ability of human FAM3C to regulate the level of plasma glucose was tested as follows. rAAV expressing human FAM3C was injected through the tail vein into mice that had been on high fat diet for eight weeks. Two weeks after the injection, 4-hour fasting blood glucose levels were determined in tail blood. In FIG. 7, "Chow" refers to lean mice on chow diet, "GFP" to DIO mice that were injected with $1 \times 10^{12}$ genome copies ("1E+12" "GC") of rAAV expressing green fluorescent protein (GFP), "hFAM3C" to mice injected with 1E+12GC of rAAV expressing human FAM3C (n=5 mice per group). As seen in FIG. 7, recombinant AAV expressing human FAM3C reduced blood glucose in DIO mice.

Example 10

Effect of Human FAM3C Expression on Serum Insulin Levels in Mice with Diet-Induced Obesity The ability of human FAM3C to relieve hyperinsulinemia in mice with diet-induced obesity was tested. rAAV expressing human FAM3C was injected through the tail vein into mice that had been on high fat diet for eight weeks. At the two and four week time points after the AAV injection, tail blood was collected from mice that had been fasting for four hours, and serum insulin was determined by ELISA. In FIG. 8, "Chow" refers to lean mice on chow diet; "GFP" to DIO mice that were injected with 1E+12 GC of rAAV expressing green fluorescent protein, and "hFAM3C" to mice injected with 1E+12 GC of rAAV expressing human FAM3C (n=5 mice per group). As seen in FIG. 8, recombinant AAV expressing human FAM3C relieved hyperinsulinemia in DIO mice.

Example 11

Effect of Human FAM3C Expression on Glucose Tolerance in Mice with Diet-Induced Obesity The ability of human FAM3C to improve glucose tolerance of mice with diet-induced obesity was evaluated as follows. rAAV expressing human FAM3C was injected through the tail vein into mice that had been on high fat diet for eight weeks. A glucose tolerance test was performed three weeks after the AAV injection. Mice fasted overnight received 1 g/kg of glucose in phosphate buffered saline (PBS) via intraperitoneal (i.p.) injection. Blood glucose levels were determined at times indicated. In FIG. 9, "Chow" refers to lean mice on chow diet; "GFP" refers to DIO mice that were injected with 1E+12 GC of rAAV expressing green fluorescent protein, and "hFAM3C" to mice injected with 1E+12 GC of rAAV expressing human FAM3C (n=5 mice per group). As seen in FIG. 9, recombinant AAV expressing human FAM3C was able to improve glucose tolerance in DIO mice.

Example 12

Effect of Human FAM3C Expression on Insulin Sensitivity in Mice with Diet-Induced Obesity The ability of human FAM3C to improve insulin sensitivity of mice with diet-induced obesity was evaluated as follows. rAAV expressing human FAM3C was injected through the tail vein into mice that had been on high fat diet for eight weeks. An insulin tolerance test was performed five weeks after the AAV injection. Glucose levels were monitored after an intraperitoneal injection of insulin (0.75 units/kg). Response to insulin was compared among DIO mice injected with AAV expressing human FAM3C and GFP by measuring blood glucose levels at times indicated. In FIG. 10 "GFP" refers to DIO mice that were injected with 1E+12 GC of rAAV expressing green fluorescent protein, and "hFAM3C" to mice injected with 1E+12 GC of rAAV expressing human FAM3C (n=5 mice per group). As seen in FIG. 10, recombinant AAV expressing human FAM3C was able to improve insulin sensitivity in DIO mice.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of treating a subject comprising:
administering to said subject having a glucose metabolism disorder a therapeutically effective amount of a protein comprising at least 90% amino acid sequence identity to an amino acid sequence of human FAM3C, wherein said administering is effective to treat a symptom of the glucose metabolism disorder.

2. The method of claim 1, wherein said glucose metabolism disorder comprises hyperglycemia and wherein said administering reduces plasma glucose in said subject.

3. The method of claim 1, wherein said glucose metabolism disorder comprises hyperinsulinemia and wherein said administering reduces plasma insulin in said subject.

4. The method of claim 1, wherein said glucose metabolism disorder comprises glucose intolerance and wherein said administering increases glucose tolerance in said subject.

5. The method of claim 1, wherein said glucose metabolism disorder comprises diabetes mellitus.

6. The method of claim 1, wherein said subject is obese.

7. The method of claim 1, wherein said glucose metabolism disorder is diet-induced.

8. The method of claim 1, wherein said subject is human.

9. The method of claim 1, wherein said administering is by parenteral injection.

10. The method of claim 9, wherein said parenteral injection is subcutaneous.

11. The method of claim 1, wherein said protein is administered in an amount of from about 0.1 µg/kg to about 1 mg/kg.

12. The method of claim 1, wherein said protein is administered in an amount of from about 0.1 µg/kg to about 1 µg/kg.

* * * * *

SEQUENCE LISTING

<160> NUMBER OF SEQ ID NOS: 17

<210> SEQ ID NO 1
<211> LENGTH: 5
<212> TYPE: PRT
<213> ORGANISM: Artificial Sequence

```
<220> FEATURE:
<223> OTHER INFORMATION: Synthetic linker

<400> SEQUENCE: 1

Gly Ser Gly Gly Ser
 1               5

<210> SEQ ID NO 2
<211> LENGTH: 4
<212> TYPE: PRT
<213> ORGANISM: Artificial Sequence
<220> FEATURE:
<223> OTHER INFORMATION: Synthetic linker

<400> SEQUENCE: 2

Gly Gly Gly Ser
 1

<210> SEQ ID NO 3
<211> LENGTH: 4
<212> TYPE: PRT
<213> ORGANISM: Artificial Sequence
<220> FEATURE:
<223> OTHER INFORMATION: Synthetic linker

<400> SEQUENCE: 3

Gly Gly Ser Gly
 1

<210> SEQ ID NO 4
<211> LENGTH: 5
<212> TYPE: PRT
<213> ORGANISM: Artificial Sequence
<220> FEATURE:
<223> OTHER INFORMATION: Synthetic linker

<400> SEQUENCE: 4

Gly Gly Ser Gly Gly
 1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic linker

<400> SEQUENCE: 5

Gly Ser Gly Ser Gly
 1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic linker

<400> SEQUENCE: 6

Gly Ser Gly Gly Gly
 1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic linker
```

-continued

<400> SEQUENCE: 7

Gly Gly Gly Ser Gly
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic linker

<400> SEQUENCE: 8

Gly Ser Ser Ser Gly
1               5

<210> SEQ ID NO 9
<211> LENGTH: 684
<212> TYPE: DNA
<213> ORGANISM: Mus musculus

<400> SEQUENCE: 9

```
atgagggtag caggagctgc aaagttggta gtggccgtgg cagtattctt actgaccttc      60
tatgttattt ctcaagtatt tgaaattaaa atggatgcaa gtttaggaaa tctatttgct     120
cgatccgcgc tggactcagc cattcgttct acgaaacctc cgaggtacaa gtgtgggatc     180
tcaaaggcgt gcccagagaa gcattttgct tttaagatgg ctagtggagc agccaatgtc     240
gtgggaccca agatctgcct ggaggacaat gttttgatga gtggtgtgaa gaataatgtc     300
ggaagaggaa tcaatattgc cttggtaaat gggaaaacag gggaagtaat agacaccaaa     360
tttttttgaca tgtggggagg agatgtggca ccattcattg agttttttgaa gaccatacaa     420
gacggaacag tagtgctaat ggctacatac gatgatggag caaccaaaact cacggatgag     480
gcacggcggc tcattgctga actgggcagc acttcgatca ccagtcttgg tttccgagat     540
aactgggtct tctgtggtgg gaagggcatt aagacaaaga gtccctttga acagcacata     600
aagaacaata ggaaacgaa caagtacgag ggatggcctg aggtggtgga gatggaagga     660
tgtatccccc agaagcaaga ctga                                            684
```

<210> SEQ ID NO 10
<211> LENGTH: 227
<212> TYPE: PRT
<213> ORGANISM: Mus musculus

<400> SEQUENCE: 10

Met Arg Val Ala Gly Ala Ala Lys Leu Val Ala Val Ala Val Phe
1               5                   10                  15

Leu Leu Thr Phe Tyr Val Ile Ser Gln Val Phe Glu Ile Lys Met Asp
            20                  25                  30

Ala Ser Leu Gly Asn Leu Phe Ala Arg Ser Ala Leu Asp Ser Ala Ile
        35                  40                  45

Arg Ser Thr Lys Pro Pro Arg Tyr Lys Cys Gly Ile Ser Lys Ala Cys
    50                  55                  60

Pro Glu Lys His Phe Ala Phe Lys Met Ala Ser Gly Ala Ala Asn Val
65                  70                  75                  80

Val Gly Pro Lys Ile Cys Leu Glu Asp Asn Val Leu Met Ser Gly Val
                85                  90                  95

Lys Asn Asn Val Gly Arg Gly Ile Asn Ile Ala Leu Val Asn Gly Lys
            100                 105                 110

-continued

```
Thr Gly Glu Val Ile Asp Thr Lys Phe Phe Asp Met Trp Gly Gly Asp
            115                 120                 125

Val Ala Pro Phe Ile Glu Phe Leu Lys Thr Ile Gln Asp Gly Thr Val
        130                 135                 140

Val Leu Met Ala Thr Tyr Asp Asp Gly Ala Thr Lys Leu Thr Asp Glu
145                 150                 155                 160

Ala Arg Arg Leu Ile Ala Glu Leu Gly Ser Thr Ser Ile Thr Ser Leu
                165                 170                 175

Gly Phe Arg Asp Asn Trp Val Phe Cys Gly Lys Gly Ile Lys Thr
            180                 185                 190

Lys Ser Pro Phe Glu Gln His Ile Lys Asn Asn Lys Thr Asn Lys
        195                 200                 205

Tyr Glu Gly Trp Pro Glu Val Val Glu Met Gly Cys Ile Pro Gln
    210                 215                 220

Lys Gln Asp
225
```

<210> SEQ ID NO 11
<211> LENGTH: 21
<212> TYPE: DNA
<213> ORGANISM: Artificial Sequence
<220> FEATURE:
<223> OTHER INFORMATION: Synthetic primer

<400> SEQUENCE: 11
atgagggtag caggagctgc a                                             21

<210> SEQ ID NO 12
<211> LENGTH: 21
<212> TYPE: DNA
<213> ORGANISM: Artificial Sequence
<220> FEATURE:
<223> OTHER INFORMATION: Synthetic primer

<400> SEQUENCE: 12
tcagtcttgc ttctggggga t                                             21

<210> SEQ ID NO 13
<211> LENGTH: 21
<212> TYPE: DNA
<213> ORGANISM: Artificial Sequence
<220> FEATURE:
<223> OTHER INFORMATION: Synthetic primer

<400> SEQUENCE: 13
atgagggtag caggtgctgc a                                             21

<210> SEQ ID NO 14
<211> LENGTH: 21
<212> TYPE: DNA
<213> ORGANISM: Artificial Sequence
<220> FEATURE:
<223> OTHER INFORMATION: Synthetic primer

<400> SEQUENCE: 14
ttagtcttgc ttctggggga t                                             21

<210> SEQ ID NO 15
<211> LENGTH: 684
<212> TYPE: DNA
<213> ORGANISM: Homo sapiens

<400> SEQUENCE: 15

```
atgagggtag caggtgctgc aaagttggtg gtagctgtgg cagtgttttt actgacattt    60
tatgttattt ctcaagtatt tgaaataaaa atggatgcaa gtttaggaaa tctatttgca   120
agatcagcat tggacacagc tgcacgttct acaaagcctc ccagatataa gtgtgggatc   180
tcaaaagctt gccctgagaa gcattttgct tttaaaatgg cagtggagc agccaacgtg    240
gtgggaccca aaatctgcct ggaagataat gttttaatga gtggtgttaa gaataatgtt   300
ggaagaggga tcaatgttgc cttggcaaat ggaaaaacag agaagtatt agacactaaa    360
tattttgaca tgtggggagg agatgtggca ccatttattg agtttctgaa ggccatacaa   420
gatgaacaa tagttttaat gggaacatac gatgatggag caaccaaact caatgatgag    480
gcacggcggc tcattgctga tttggggagc acatctatta ctaatcttgg ttttagagac   540
aactgggtct tctgtggtgg aagggcatt aagacaaaaa gcccttttga acagcacata    600
aagaacaata aggatacaaa caaatatgaa ggatggcctg aagttgtaga aatggaagga   660
tgcatccccc agaagcaaga ctaa                                          684
```

<210> SEQ ID NO 16
<211> LENGTH: 227
<212> TYPE: PRT
<213> ORGANISM: Homo sapiens

<400> SEQUENCE: 16

```
Met Arg Val Ala Gly Ala Ala Lys Leu Val Val Ala Val Ala Val Phe
 1               5                  10                  15

Leu Leu Thr Phe Tyr Val Ile Ser Gln Val Phe Glu Ile Lys Met Asp
            20                  25                  30

Ala Ser Leu Gly Asn Leu Phe Ala Arg Ser Ala Leu Asp Thr Ala Ala
        35                  40                  45

Arg Ser Thr Lys Pro Pro Arg Tyr Lys Cys Gly Ile Ser Lys Ala Cys
    50                  55                  60

Pro Glu Lys His Phe Ala Phe Lys Met Ala Ser Gly Ala Ala Asn Val
65                  70                  75                  80

Val Gly Pro Lys Ile Cys Leu Glu Asp Asn Val Leu Met Ser Gly Val
                85                  90                  95

Lys Asn Asn Val Gly Arg Gly Ile Asn Val Ala Leu Ala Asn Gly Lys
           100                 105                 110

Thr Gly Glu Val Leu Asp Thr Lys Tyr Phe Asp Met Trp Gly Gly Asp
       115                 120                 125

Val Ala Pro Phe Ile Glu Phe Leu Lys Ala Ile Gln Asp Gly Thr Ile
   130                 135                 140

Val Leu Met Gly Thr Tyr Asp Asp Gly Ala Thr Lys Leu Asn Asp Glu
145                 150                 155                 160

Ala Arg Arg Leu Ile Ala Asp Leu Gly Ser Thr Ser Ile Thr Asn Leu
                165                 170                 175

Gly Phe Arg Asp Asn Trp Val Phe Cys Gly Gly Lys Gly Ile Lys Thr
            180                 185                 190

Lys Ser Pro Phe Glu Gln His Ile Lys Asn Lys Asp Thr Asn Lys
        195                 200                 205

Tyr Glu Gly Trp Pro Glu Val Val Glu Met Glu Gly Cys Ile Pro Gln
    210                 215                 220

Lys Gln Asp
225
```

<210> SEQ ID NO 17
<211> LENGTH: 227

```
<212> TYPE: PRT
<213> ORGANISM: Bos taurus

<400> SEQUENCE: 17

Met Arg Val Ala Gly Ala Ala Lys Leu Val Val Ala Val Ala Val Phe
  1               5                  10                  15

Leu Leu Thr Phe Tyr Val Ile Ser Gln Val Phe Glu Ile Lys Met Asp
             20                  25                  30

Ala Ser Leu Gly Asn Leu Phe Ala Arg Ser Ala Leu Asp Ala Val Val
         35                  40                  45

Arg Ser Thr Lys Pro Pro Arg Tyr Lys Cys Gly Ile Ser Lys Ala Cys
     50                  55                  60

Pro Glu Lys His Phe Ala Phe Lys Met Ala Ser Gly Ala Ala Asn Val
 65                  70                  75                  80

Val Gly Pro Lys Ile Cys Leu Glu Asp Asn Val Leu Met Ser Gly Val
                 85                  90                  95

Lys Asn Asn Val Gly Arg Gly Ile Asn Val Ala Leu Val Asn Gly Lys
                100                 105                 110

Thr Gly Glu Leu Ile Asp Thr Arg Phe Phe Asp Met Trp Gly Gly Asn
            115                 120                 125

Val Ala Pro Phe Ile Glu Phe Leu Lys Ala Ile Gln Asp Gly Thr Ile
        130                 135                 140

Val Leu Met Gly Thr Tyr Asp Asp Gly Ala Thr Lys Leu Asn Asp Glu
145                 150                 155                 160

Ala Arg Arg Leu Ile Ala Glu Leu Gly Ser Thr Ser Ile Thr His Leu
                165                 170                 175

Gly Phe Arg Asp Asn Trp Val Phe Cys Gly Gly Lys Gly Ile Lys Thr
            180                 185                 190

Lys Ser Pro Phe Glu Gln His Ile Lys Asn Asn Lys Asp Thr Asn Lys
        195                 200                 205

Tyr Glu Gly Trp Pro Glu Val Val Glu Met Glu Gly Cys Ile Pro Gln
    210                 215                 220

Lys Gln Asp
225
```